United States Patent
Wang et al.

(10) Patent No.: US 8,280,001 B2
(45) Date of Patent: Oct. 2, 2012

(54) RADIATION SCULPTING BY COORDINATING ROTATION OF FIXED BEAMS AND MOTION OF PATIENT SUPPORT SYSTEM

(75) Inventors: Chao Wang, Columbia, MD (US); Xinsheng Cedric Yu, Clarksville, MD (US)

(73) Assignee: Xcision Medical Systems LLC, Clarksville, MD (US)

( * ) Notice: Subject to any disclaimer, the term of this patent is extended or adjusted under 35 U.S.C. 154(b) by 117 days.

(21) Appl. No.: 12/723,642

(22) Filed: Mar. 13, 2010

(65) Prior Publication Data
US 2011/0222660 A1 Sep. 15, 2011

(51) Int. Cl.
*A61N 5/10* (2006.01)
*G21K 1/02* (2006.01)
(52) U.S. Cl. .......................................... 378/65; 378/147
(58) Field of Classification Search .................... 378/20, 378/68, 195, 208, 65, 147; 29/428
See application file for complete search history.

(56) References Cited

U.S. PATENT DOCUMENTS

| 2008/0226030 A1 | 9/2008 | Otto |
| 2008/0317202 A1 | 12/2008 | Partain et al. |
| 2009/0316858 A1 | 12/2009 | Nord et al. |

OTHER PUBLICATIONS

Int'l Search Report & Written Opinion issued in appl. No. PCT/US11/28253 (2011).

*Primary Examiner* — Irakli Kiknadze
(74) *Attorney, Agent, or Firm* — Carol Larcher; Larcher & Chao Law Group

(57) ABSTRACT

A method of irradiating a target tissue in a patient comprising positioning the patient on a patient support system so that the target tissue in the patient is within irradiating distance of at least one source of a beam of radiation and moving the patient support system relative to the at least one source of a beam of radiation and, coordinately with movement of the patient support system, rotating the at least one source of radiation relative to the target tissue, which comprises and/or is adjacent to a non-target tissue, so that the center of rotation of the beam of radiation is placed at one or more desired locations within the target tissue, while simultaneously and/or sequentially irradiating the target tissue; a collimator; a method of making such a collimator; a system for irradiating a target tissue in a patient; and a method of planning irradiation of a target tissue in a patient.

10 Claims, 15 Drawing Sheets a)

b)

c)

d)

Representative Parametric
Points $b^n(t)$

RADIATION SCULPTING BY COORDINATING ROTATION OF FIXED BEAMS AND MOTION OF PATIENT SUPPORT SYSTEM

TECHNICAL FIELD

The present disclosure relates to a method and a system for delivering radiation to a target tissue, such as a target tissue that comprises and/or is adjacent to a non-target tissue.

BACKGROUND

Radiation therapy and radiosurgery are established methods of treating patients with certain malignant and benign diseases. Radiation therapy, which is also referred to as radiotherapy, radiation oncology, and XRT, involves the administration of ionizing radiation to a patient, such as a patient being treated for cancer. Exposure of malignant cells to radiation inhibits their proliferation and induces cell death. A patient undergoing radiation therapy for cancer treatment is typically treated with ionizing radiation many times, often at defined intervals. A disadvantage of radiation therapy is that normal cells and tissues may be adversely affected by the radiation. Assuming that normal tissue recovers at a faster rate than cancerous tissue, administration of radiation at defined intervals is expected to allow any normal tissue, which has been adversely affected by the radiation, to recover before the next treatment. Radiation therapy also may be combined with surgery, chemotherapy, and/or hormone therapy. Radiation therapy is also used to treat various non-malignant conditions, such as trigeminal neuralgia, severe thyroid eye disease, pterygium, and pigmented villonodular synovitis, and to inhibit keloid scar growth and heterotopic ossification. However, the use of radiation therapy to treat non-malignant conditions is limited by the risk of radiation-induced cancer.

Multileaf collimators have been used with linear accelerators (LINAC) to improve the geometric conformation of the radiation treatment to the target tissue as a way of minimizing adverse effects on normal tissue. Multileaf collimators have many rectangular vanes or "leaves" of a material having a high atomic number, such as tungsten, that can be moved independently in and out of the path of a particle beam. When a "leaf" is in the path of a particle beam, the beam is blocked. Therefore, by positioning the "leaves" to form an aperture having a specific geometry, it is possible to shape a beam of radiation to conform to a desired geometric shape. Intensity modulated radiation therapy (IMRT) further improves the conformation by using multiple weighted apertures for each treatment beam to account for geometric variations in the dimensions of the beam projection.

Radiosurgery is a medical procedure that allows non-invasive treatment of benign and malignant tumors and other conditions, such as arteriovenous malformations (AVMs) and trigeminal neuralgia. It involves precisely directing highly focused beams of ionizing radiation at a single point (referred to as an "isocenter"). By applying a precise dosage of radiation to the isocenter, tumors and other lesions, which are otherwise inaccessible or inadequate for open surgery, can be ablated. Typically, only a single or a few treatments are necessary. Radiosurgery typically involves the use of multiple small circular collimated radiation beams directed at the isocenter. Consequently, radiation is concentrated at the isocenter through the superposition of multiple small overlapping beams. Adjacent tissues, which are not in the isocenter, are not exposed to the overlapping beams and, therefore, are not subjected to the concentrated dose of radiation.

The multiple overlapping beams may be created using many individual sources of radiation with individual collimators, such as in the case of the GammaKnife™ from Elekta (Stockholm, Sweden), or by arcing a single source and collimator about a point. Traditional isocentrically mounted medical LINACs achieve a similar effect of multiple independent beams using a combination of table and gantry angles with circular or multileaf collimators.

A complex tissue volume can be treated with radiosurgery using multiple isocenters (or "shots") at discrete points inside the volume. Radiation is delivered to each isocenter with a specific arrangement of multiple beams and a specific collimator size.

The dose of radiation used in radiation therapy and radiosurgery is limited by concerns over toxicity to non-target tissue, i.e., normal tissue, within and/or adjacent to the target tissue, e.g., diseased tissue. The amount of radiation to which non-target tissue is exposed is determined by a number of factors. For example, there is a margin of error associated with the placement of the radiation beam, which is limited by the mechanical accuracy of the treatment device and the knowledge of where the non-target tissue is at the time of treatment. The nature and properties of a single divergent beam of radiation incident on the target tissue also impact the exposure of non-target tissue to radiation. The lateral range of secondary electrons outside the field of radiation, the physical size and shape of the source of the photons, the shape of the collimator edge, photon scatter, and transmission through the collimator affect the fall-off in dosage (i.e., the penumbra of the radiation beam) of high-energy photon radiation away from the edge of the collimator. The interaction of all beams also impacts the exposure of non-target tissue to radiation. Geometrically, all beams overlap in the target tissue, and they also may overlap in the non-target tissue. Such overlap in the target tissue and the non-target tissue makes it very difficult, if not impossible, to deliver a uniformly high dose of radiation to the target tissue while not delivering any radiation to the non-target tissue. Away from the edge of the target tissue, e.g., the tumor, the dose of radiation will also fall off with a varying gradient rather than abruptly. Depending on the techniques used, including the collimator design and the beam arrangement, such dose fall-off can be very steep or very gentle. Such dose fall-off at the target boundary is referred to as the "dose gradient." The best therapeutic gain can be achieved with a high dose gradient at the edge of the target tissue. For a single divergent high-energy photon beam of radiation covering the target tissue, the "dulling" of dose gradient is caused by scattered photons and electrons along the radial dimension of the beam boundary and the beam's entrance and exit along the beam direction. With multiple beams, the dose gradient is largely influenced by the overlap of beams on the entry and exit sides of the target tissue. The divergence of radiation beams also contributes to making the dose gradient less steep. The use of multiple focal spots (also referred to as "shots"), such as when a volume of target tissue cannot be treated with a single isocenter, results in interaction of beams from adjacent focal spots. Interaction of beams from adjacent focal spots can increase the exposure of non-target tissue within and/or adjacent to the target tissue to radiation.

The main reason why the above methods result in exposure of non-target tissue to radiation is that the methods cannot create a sharp dose gradient at the boundary of a target tissue. The collimating systems are designed to treat targets of all sizes and shapes. With medical LINACs, the collimators are either fixed or dynamically configurable. Fixed collimators are invariably circular in shape. Dynamically configurable collimators are either composed of four jaws, which can shape any rectangular field, or use multiple leaves of varying thickness, which can shape irregular fields. Because target tissues, such as tumors, are rarely rectangular, the jaws have gradually become obsolete. For multileaf collimators, the beam boundary cannot be very sharp no matter how thin the leaves are. For ablative treatments, circular collimators are typically used. A circular collimator, however, cannot create a sharp dose fall-off between a target tissue and an adjacent non-target tissue when beams are overlapped to form an edge. This is illustrated in FIG. 2a and FIG. 2c. FIG. 2a is a schematic drawing of the movement of a cylindrical radiation beam along a linear interface (see "Brief Description of the Figures" for details). FIG. 2c is a graph of the cumulative radiation intensity ("I") versus the location along the central axis of overlap between the adjacent cylindrical radiation beams ("y") of FIG. 2a (see "Brief Description of the Figures" for details). As can be seen in FIG. 2c, the dose fall-off from the central axes and the outer edges of the cylindrical radiation beam along the central axis of overlap between adjacent cylindrical radiation beams is from about 95% to about 5%, which is on the order of the radius of the collimated beam. In other words, a circular collimator makes a "dull" knife for sculpting. External beam radiation therapy typically achieves a dose fall-off of about 90% to about 10% over about 10 mm, whereas radiosurgery with an ablative system typically achieves a dose fall-off of about 90% to about 10% over about 5 mm. Fixed collimators are advantageous in that they have small beam penumbra and precise divergence.

Moving a circular beam along a line is a special case. In general, beams are overlapped to shape curved surfaces in two dimensions as illustrated in FIG. 3a and FIG. 3c. FIG. 3a is a schematic drawing of the movement of a cylindrical radiation beam along a convex interface (see "Brief Description of the Figures" for details). FIG. 3c is a graph of the cumulative radiation intensity ("I") versus the location along the radial dimension ("r") of FIG. 3a (see "Brief Description of the Figures" for details). As can be seen in FIG. 3c, a circular collimator cannot form a completely "cold" (low dose) hole surrounded by "hot" (high dose) regions.

In addition to the above, a patient is held stationary on a patient support system, such as a table, during radiation treatment, and the radiation beam is moved by moving the collimator. The radiation beam can be rotated around the patient with a single isocenter. There is no dynamic coordination of the patient support system with the dynamic delivery of the radiation beam. The only known exception is the management of breathing-induced tumor motion by moving the patient support system exactly opposite that of the tumor in order to keep the tumor location stationary in space (D'Souza et al., "Intra-Fraction Motion Synchronized Adaptive Couch-Based Radiation Delivery: A Feasibility Study," Phys. Med. Biol. 50: 4021-4033 (2005)).

Radiation therapy using external beams as described above typically places the tumor at the isocenter, i.e., the intersection of all rotational axes. This arrangement makes patient set-up much easier. However, in any beam direction, radiation can only be directed at a point in the target tissue through one unique path. This significantly limits how the target tissue is irradiated.

Some degree of freedom is possible with CyberKnife (Accuray Inc., Sunnyvale, Calif.). With CyberKnife, an x-band LINAC is mounted on a 6-axes robot, and the patient is kept stationary on a patient support system. Using circular collimators, CyberKnife delivers radiation doses to the target tissue by crossing many (e.g., a hundred or more), variously oriented, cylindrical radiation beams, which do not share a common center of rotation and, therefore, are not isocentric, in the target. While variously angled cylindrical radiation beams can be realized with the CyberKnife, configuring the beams can be complex and, since it involves the use of a robot, expensive. Furthermore, CyberKnife can only use a single source of radiation, which requires more time to treat a patient, and, since CyberKnife uses circular collimators, it cannot create a sharp dose fall-off between a target tissue and an adjacent non-target tissue when beams are overlapped to form an edge.

The present disclosure seeks to overcome the disadvantages inherent in currently available methods of radiation therapy. In view of this, it is an object of the present disclosure to provide a method, a collimator, and a system for dynamically sculpting target tissue so that the radiation doses at the boundaries of the target tissue and any non-target tissue(s) have a sharp fall-off, thereby reducing, if not eliminating, "dose spillage" to non-target tissue and delivering a uniform dose to the target tissue. Compared to currently available methods of radiation therapy, the method of the present disclosure is easier to use and more economical. It is another object of the present disclosure to provide a method of planning irradiation of a target tissue in accordance with the present disclosure. These and other objects and advantages, as well as inventive features, will become apparent from the detailed description provided herein.

SUMMARY

A method of irradiating a target tissue in a patient is provided. The method comprises positioning the patient on a patient support system so that the target tissue in the patient is within irradiating distance of at least one source of a beam of radiation and moving the patient support system relative to the at least one source of a beam of radiation and, coordinately with movement of the patient support system, rotating the at least one source of radiation relative to the target tissue, which comprises and/or is adjacent to a non-target tissue, so that the center of rotation of the beam of radiation is placed at one or more desired locations within the target tissue, while simultaneously and/or sequentially irradiating the target tissue. The beam of radiation can have a D-shaped cross-section, in which case the straight edge of the D-shaped cross-section of the beam of radiation is placed tangentially to the boundary of the target tissue and the non-target tissue as the beam is rotated.

A collimator, in particular a collimator with a fixed opening and divergence, is also provided. The collimator (a) shapes a beam of radiation to have a D-shaped cross-section, (b) maintains the central axis of the beam of radiation on or adjacent to the straight edge of the D-shaped cross-section of the beam of radiation, and (c) can fully rotate the beam of radiation in either direction about the beam axis, such that the straight edge of the D-shaped cross-section of the beam of radiation can face any direction.

Further provided is a method of making a collimator. The method comprises joining half of a circular (cross-section) collimator with a cone-shaped tunnel with half of a rectangular (cross-section) collimator with a pyramid-shaped tunnel, where both of the circular collimator and the rectangular collimator have the same divergence.

Further provided is a system for irradiating a target tissue in a patient. The system comprises (i) a patient support system, which comprises (a) a table or a couch, either of which is optionally padded, (b) one, two or three motors, each of which drives movement of the table or the couch in the direction of a separate axis, (c) optionally, a base, in which case the one or more motors can be housed in the base, and (d) a computerized control system, which can control the movement of the patient support system; (ii) at least one rotatable source of a beam of radiation, wherein each source of a rotatable beam of radiation can be rotated around a target tissue in a patient positioned on the patient support system; (iii) at least one collimator, wherein each collimator is operably aligned with one rotatable source of a beam of radiation; and (iv) a central control unit, which can execute a patient treatment plan including rotation of at least one rotatable source of a beam of radiation relative to a target tissue in a patient positioned on a patient support system, rotation of the at least one rotatable source of a beam of radiation, and movement of a patient support system. Preferably, the at least one collimator (a) shapes the beam of radiation to have a D-shaped cross-section, (b) maintains the central axis of the beam of radiation on or adjacent to the straight edge of the D-shaped cross-section of the beam of radiation, and (c) can fully rotate the D-shaped cross-section of the beam of radiation in either direction, such that the straight edge of the D-shaped cross-section of the beam of radiation can face any direction.

Still further provided is a method of planning irradiation of a target tissue in a patient with a system for irradiating a target tissue in a patient. The method comprises: i) determining the volume and the surface contour of the target tissue to be irradiated and, if present, the volume and the surface contour of a non-target tissue located wholly within the target tissue and/or the surface contour and, optionally, the volume of a non-target tissue located partially within the target tissue, (ii) setting the radiation dose to be delivered to the target tissue and limiting the radiation dose to the non-target tissue, (iii) assigning control points to the surface contours identified in (i), (iv) determining the angle of the beam of radiation, the orientation of the collimator, and the position of the patient support system at each control point, (v) assigning "wild card" points within the volume of the target tissue with the proviso that a "wild card" point is not assigned within the volume of any non-target tissue that is located wholly or partially within the target tissue, (vi) determining the path of motion when all control points and, optionally, one or more "wild card" points, are connected and optimizing the weighting of each beam of radiation so as to provide a uniform dose of radiation within the target tissue and a sharp drop-off away from the boundary between the target tissue and any non-target tissue, and (vii) checking the resulting radiation dose distribution against a desired radiation dose distribution and adjusting the path of motion and the weightings of control points accordingly, and, if needed, adding more control points.

DETAILED DESCRIPTION

Figure 1:
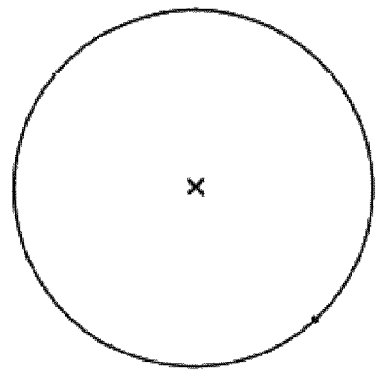
FIG. 1a is a schematic drawing of a single radiation beam with a circular field, the central axis of which is indicated with an "x." This beam is referred to herein as a "circular radiation beam."
FIG. 1b is a schematic drawing of the cross-section of a single D-shaped radiation beam, the central axis of which is indicated with an "x." In a preferred embodiment and for the purpose of illustration, the "D" shaped cross section is formed by joining a half circle and a narrow rectangle at the dashed line.
FIG. 1c is a drawing of the beam intensity profile associated with the single circular radiation beam of FIG. 1a, wherein the vertical line indicates the beam intensity at the central axis.
FIG. 1d is a drawing of the beam intensity profile associated with the single D-shaped radiation beam of FIG. 1b, wherein the vertical line indicates the beam intensity at the central axis.
Figure 1:
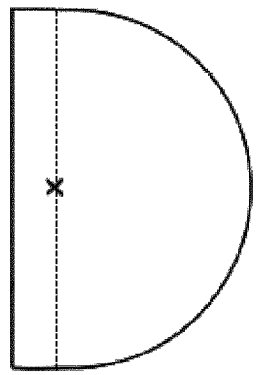
Figure 1:
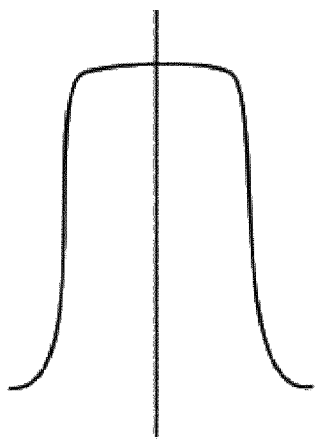
Figure 1:
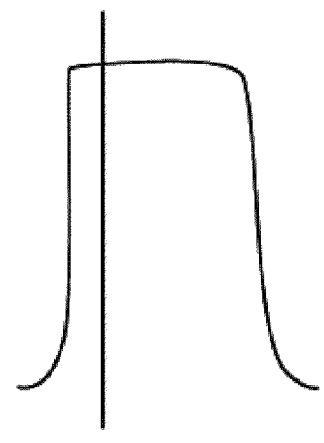

The present disclosure does not use a single fixed isocenter and a stationary patient support system. Although the collimator and the beams of radiation still rotate around a point, the point is not fixed in relation to the patient. Coordinated motion of a patient support system and rotation of a beam of radiation enables a target tissue in a patient to be traversed by beams of radiation from any orientation, allowing much greater freedom than current radiation treatment equipment that uses a fixed isocenter relative to the patient's anatomy to create overlapping, traversing patterns similar to line art. By coordinating beam rotation and patient movement, such as in all three dimensions, radiation can hit every point in the target from all co-planar directions, if the rotation is coplanar, or from all non-colliding directions, if rotation of the beam is non-coplanar.

In view of the foregoing, the present disclosure provides a method of irradiating a target tissue in a patient. The method comprises positioning the patient on a patient support system so that the target tissue in the patient is within irradiating distance of at least one source of a beam of radiation and moving the patient support system, such as in three dimensions, relative to the at least one source of a beam of radiation and, coordinately with movement of the patient support system, rotating the at least one source of radiation relative to the target tissue, which comprises and/or is adjacent to a non-target tissue, so that the center of rotation of the beam of radiation is placed at one or more desired locations within the target tissue, while simultaneously and/or sequentially irradiating the target tissue.

"Target tissue" refers to any tissue intended to be irradiated in accordance with the present disclosure. It is anticipated that, at least in some instances, the target tissue will be a malignant tumor. "Non-target tissue" refers to any tissue that is not intended to be irradiated. Non-target tissue can be adjacent to and/or surround a target tissue. Alternatively or additionally, non-target tissue can be located anywhere within the target tissue and can occupy varying volume(s) of the target tissue. For example, the urethra can be surrounded by prostate tissue containing cancer. It is anticipated that the non-target tissue typically will be normal and, in at least some instances, may comprise one or more tissues or structures, such as an organ, that can be critical for the health of the patient and, therefore, should be avoided (an "avoidance structure").

Any suitable patient support system that enables movement of the patient, such as in all three dimensions, can be used in the context of the method. An example is a patient support system, such as a padded table or a couch, the position of which can be driven by one, two or three motors, e.g., analog or digital motors, so that movement in at least one axis, such as the vertical axis, up to three axes of motion can be achieved. Movement in at least the vertical axis (i.e., the axis perpendicular to the top of the patient support system) is preferred. Redundant positional sensors can be used to ensure positional accuracy. The patient support system can comprise a base, in which case the motor(s) can be housed in the base. The movement of the patient support system is preferably controlled by a computerized control system.

At least one source of a beam of radiation is used. Preferably, more than one source of a beam of radiation, such as two, three, or even more, is/are used. The number of sources of beams of radiation that can be used is limited by physical space and cost limitations. When more than one source of a beam of radiation is used, patient treatment time can be reduced.

The beam of radiation can have, and preferably does have, a D-shaped cross-section. Desirably, the beam of radiation is shaped by a fixed or variable collimator, and has a D-shaped cross-section, such as that which is formed by joining a half circle with a rectangle having a length of the diameter of the half circle and a width not larger than the radius of the half circle. For ease of reference, the term "D-shaped" will be used to refer collectively to D-shaped cross-sections as well as cross-sections having more or less of a "D" shape, unless otherwise indicated or contradicted by context. A "D" shape can be formed by joining a half circle with a rectangle, which has a length equal to the diameter of the half circle and a width that is equal to or less than, even substantially less than, the radius of the half circle. Preferably, and even desirably, the straight edge of the D-shaped cross-section of the beam of radiation is placed tangentially at the boundary of the target tissue and the non-target tissue. The central axis of the D-shaped radiation beam is located on or close to the flattened portion of the "D."

In a preferred embodiment, the central axis of the beam of radiation is kept stationary, i.e., it is focused on a point that is fixed in space. The beam of radiation is rotated around the patient. The collimator is rotated as necessary to alter the orientation of the cross-section, such as a D-shaped cross-section, of a beam. Preferably, and even desirably, the straight edge of a D-shaped cross-section is placed tangentially to the boundary of the target tissue and the non-target tissue, and the tangential placement of the straight edge of the D-shaped cross-section of a beam of radiation is maintained during coordinated rotation of the at least one source of radiation relative to the target tissue and movement of the patient support system. The patient is moved (by means of the patient support system) coordinately with the beam of radiation and the angle of the collimator so that the focal point relative to the volume of the target tissue can be changed. In theory, the beam as well as the patient support system can move independently at the same time, although such an arrangement would be more difficult to implement and unnecessary.

Preferably, the movement of the patient support system, the rotation of the beam of radiation around the patient, i.e., relative to the target tissue, and the rotation of the collimator to reorient the cross-section, such as the straight edge of a D-shaped cross-section, of the beam of radiation are coordinated such that the edge of the cross-section, such as the straight edge of the "D," is kept tangentially to the surface of the target tissue or the surface of a non-target tissue that is within the target tissue and needs to be protected. Because the surface of the target tissue and the surface of the non-target tissue rarely take the shape of a perfect cylinder oriented perpendicularly to the plane of beam rotation, the collimator angle has to be changed at different beam angles in order to keep the straight edge of the "D," for example, parallel to the interface surface. As the beam is rotated around the patient, such coordination allows the beam to sculpt the volume of the target tissue and to prevent the radiation beam from directly hitting a non-target tissue that is surrounded by the target tissue.

Radiation, combined with beam rotation and patient movement, such as in all three dimensions, can traverse every spot in the volume of target tissue from all beam directions, if necessary. By allowing the radiation beam to traverse every point in the volume of target tissue from any direction, the tracks of the beams, which resemble rods with a "D"-shaped cross-section when beams of radiation having D-shaped cross-sections are used, can overlap in the target to form any desirable pattern, as in string arts.

The above method is illustrated with reference to the figures. For example, FIGS. 1a-1d compare the cross-section and beam intensity profile associated with a single circular radiation beam and a single D-shaped radiation beam. Specifically, FIG. 1a is a schematic drawing of a single radiation beam with a circular field, the central axis of which is indicated with an "x." FIG. 1b is a schematic drawing of the cross-section of a single D-shaped radiation beam, the central axis of which is indicated with an "x." FIG. 1c is a drawing of the beam intensity profile associated with the single circular radiation beam of FIG. 1a, wherein the vertical line indicates the beam intensity at the central axis. FIG. 1d is a drawing of the beam intensity profile associated with the single D-shaped radiation beam of FIG. 1b, wherein the vertical line indicates the beam intensity at the central axis. A typical collimator used in radiosurgery generates a radiation beam having a circular cross-section as shown in FIG. 1a. As shown in FIG. 1c, a radiation beam having a circular cross-section has a beam intensity profile in which the intensity of the beam falls off sharply at the beam boundary. As shown in FIG. 1d, a radiation beam having a D-shaped cross-section also has a beam intensity profile in which the intensity of the beam falls off sharply at the beam boundary, with the fall-off on the straight edge being slightly better due to the fact that the straight boundary is closer to the central axis. Therefore, when considering only single beams, there is little advantage of using a D-shaped beam over a cylindrical beam.

When using an external beam of radiation, however, one rarely focuses a single beam of radiation at a target tissue in a single orientation. A single beam, whether one having a circular cross-section or a D-shaped cross-section, generally does not fit the target tissue very well. In radiosurgery the beam size is typically smaller than the target. The use of multiple beams from different orientations, or a single beam from different orientations, allows high doses of radiation to be delivered to the target tissue, while exposing the non-target tissue(s) to as low doses of radiation as possible. In order to deliver a high dose of radiation to a target tissue, the beam would have to be moved over the area of the target tissue and kept within the boundary of the target tissue. Conventionally, this is done by making multiple rotational arcs of a beam to deliver a more or less spherically shaped, high-dose volume before the patient is moved. The task of treatment planning is to pack these "spheres" of high-dose volumes within the boundary of the target. However, in accordance with the present disclosure, movement of the beam of radiation is coordinated with movement of the patient, which abandons the conventional concept of isocenters and enables the use of numerous (e.g., two, three, or more) beams from all directions aimed at different locations in the target. With the method of the present disclosure, treatment planning is given much greater freedom to create the desired dose distribution.

Figure 2:
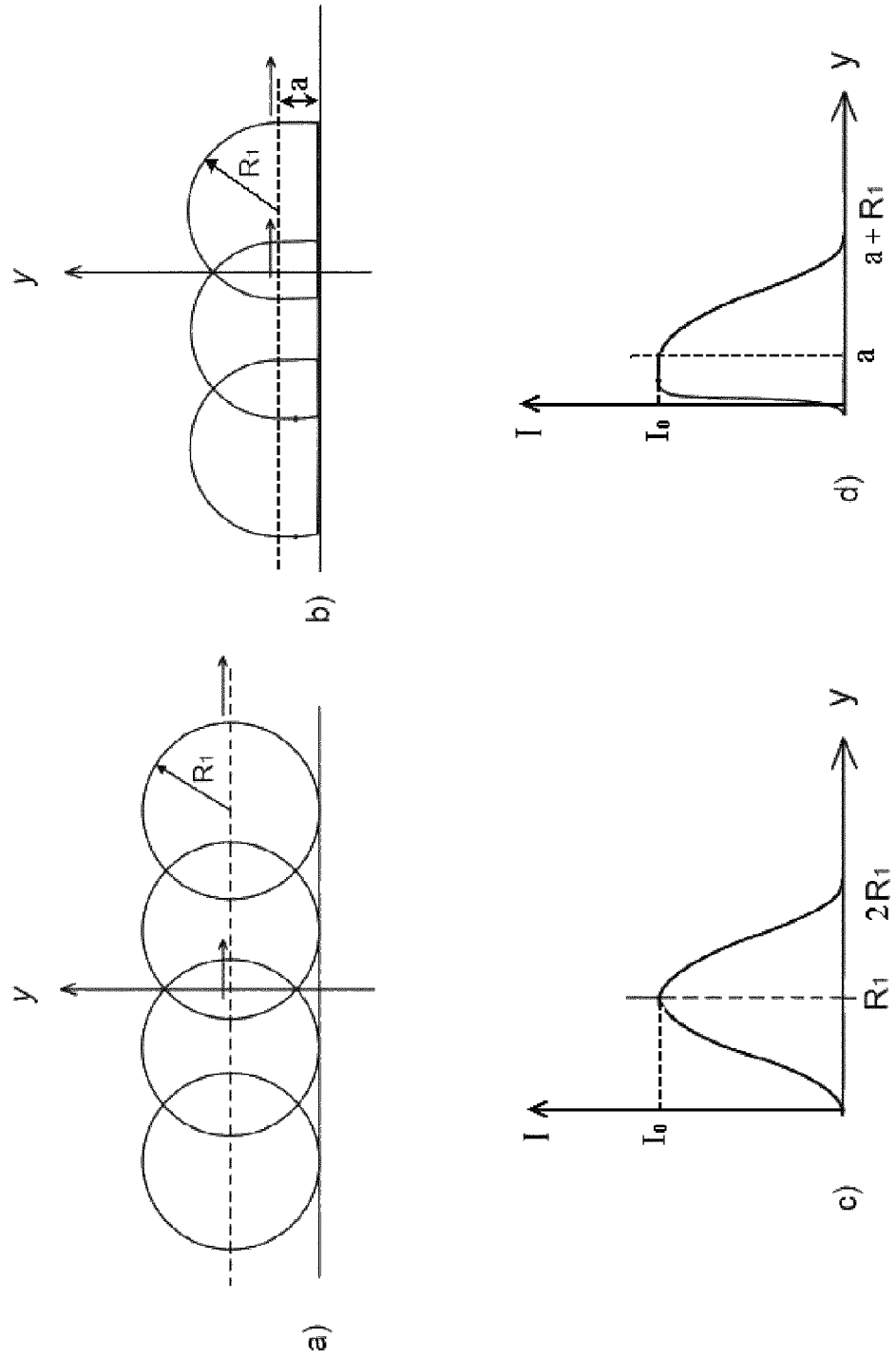
FIG. 2a is a schematic drawing of the movement of a circular radiation beam along a linear interface (the solid horizontal line; e.g., interface between target tissue and non-target tissue), wherein the continuous movement of the beam in the direction of the small horizontal arrows (→) is represented by a series of four overlapping circles, each of which represents the circumference of the cross-section of the circular radiation beam. The horizontal dotted line indicates the central axes of the circular radiation beams. The large vertical arrow (↑) labeled "y" represents the dimension perpendicular to the linear interface between the target tissue and the non-target tissue. "$R_1$" represents the radius of the circular radiation beam, which is also the distance between the central axis and the outer edge of the circular radiation beam along the "y" dimension.
FIG. 2b is a schematic drawing of the movement of a D-shaped radiation beam along a linear interface (the solid horizontal line; e.g., interface between target tissue and non-target tissue), wherein the continuous movement in the direction of the small horizontal arrows (→) is represented by a series of three overlapping "D" shapes, each of which represents the circumference of the cross-section of the D-shaped radiation beam. The horizontal dotted line indicates the central axes of the D-shaped radiation beams (i.e., where the half circle joins with the narrow rectangle). The large vertical arrow (↑) labeled "y" represents the dimension perpendicular to the linear interface between the target tissue and the non-target tissue. "$R_1$" represents the distance between the central axis and the curved edge of the D-shaped radiation beam, which is also the radius of the half-circle. "a" represents the distance between the central axis and the straight edge of the D-shaped radiation beam along the "y" dimension, which is also the width of the rectangle.
FIG. 2c is a graph of the cumulative radiation intensity ("I") vs. the distance from the linear interface between the target and the non-target tissues along the "y" dimension of FIG. 2a, wherein the central axes of the circular radiation beams are represented by a vertical dotted line, and the maximum cumulative radiation intensity is indicated by $I_0$.
FIG. 2d is a graph of the cumulative radiation intensity ("I") vs. the distance from the linear interface between the target and the non-target tissues along the "y" dimension of FIG. 2b, wherein the central axes of the D-shaped radiation beams are represented by a vertical dotted line, and the maximum cumulative radiation intensity is indicated by $I_0$.

When considering the cumulative radiation intensities of superimposing beams of radiation, the use of beams having a D-shaped cross-section is advantageous over beams having a circular cross-section. This advantage is illustrated in FIGS. 2a-2d, which compare the cross-sections and beam intensity profiles associated with the use of multiple circular radiation beams and multiple D-shaped radiation beams. FIG. 2a is a schematic drawing of the movement of a circular radiation beam along a linear interface (the solid horizontal line; e.g., interface between target tissue and non-target tissue), wherein the continuous movement of the beam in the direction of the small horizontal arrows (→) is represented by a series of four overlapping circles, each of which represents the circumference of the cross-section of the circular radiation beam. The horizontal dotted line indicates the central axes of the circular radiation beams. The large vertical arrow (↑) labeled "y" represents the dimension perpendicular to the linear interface between the target tissue and the non-target tissue. "$R_1$" represents the radius of the circular radiation beams, which is also the distance between the central axis and the outer edge of the circular radiation beam along the "y" dimension. FIG. 2b is a schematic drawing of the movement of a D-shaped radiation beam along a linear interface (the solid horizontal line; e.g., interface between target tissue and non-target tissue), wherein the continuous movement in the direction of the small horizontal arrows (→) is represented by a series of three overlapping "D" shapes, each of which represents the circumference of the cross-section of the D-shaped radiation beam. The horizontal dotted line indicates the central axes of the D-shaped radiation beams (i.e., where the half circle joins with the narrow rectangle). The large vertical arrow (↑) labeled "y" represents the dimension perpendicular to the linear interface between the target tissue and the non-target tissue. "$R_1$" represents the distance between the central axis and the curved edge of the D-shaped radiation beam, which is also the radius of the half-circle. "a" represents the distance between the central axis and the straight edge of the D-shaped radiation beam along the "y" dimension, which is also the width of the rectangle. FIG. 2c is a graph of the cumulative radiation intensity ("I") vs. the distance from the linear interface between the target tissue and the non-target tissue along the "y" dimension of FIG. 2a, wherein the central axes of the circular radiation beams are represented by a vertical dotted line, and the maximum cumulative radiation intensity is indicated by $I_0$. FIG. 2d is a graph of the cumulative radiation intensity ("I") vs. the distance from the linear interface between the target tissue and the non-target tissue along the "y" dimension of FIG. 2b, wherein the central axes of the D-shaped radiation beams are represented by a vertical dotted line, and the maximum cumulative radiation intensity is indicated by $I_0$. If a line were drawn parallel to the target boundary at a distance of y from the boundary, the line would be intersected by the cross-section of the beam (i.e., the circle or the D-shaped circumference). The length between the two points of intersection is defined as the cord length ("c"). The cumulative intensity can be expressed as $I=I_0*c/(2R_1)$, where $I_0$ is the maximum intensity at the central axis of the beam and "$R_1$" is the radius of the circle or the height of the "D". By comparing FIG. 2c with FIG. 1c and FIG. 2d with FIG. 1d, respectively, it can be seen that the dose fall-off is more gentle (i.e., less sharp) when a single beam is dynamically moved or multiple such beams are horizontally combined. By comparing FIG. 2d with FIG. 2c, it can be seen that the dose fall-off is sharp at the boundary between the target tissue and the non-target tissue when a D-shaped radiation beam is moved, whereas the dose fall-off is gentle at the boundary between the target tissue and the non-target tissue when a circular radiation beam is moved. This is why the use of circular collimators in conventional ablative radiation treatments cannot create a sharp edge along a straight line. In contrast, the use of a D-shaped collimator, in accordance with the present disclosure, can create a sharp edge along a straight line. On the other hand, the dose fall-off on the opposite side of the straight edge is just as gentle as the combination of the circular beams. This is advantageous inasmuch as it allows easier abutment of the beam with other beams and easier shaping of corners simply by rotating the "D" to face in any direction in space. Rotation of the "D" to face in any direction in space allows a target tissue with a complex volume to be sculpted and irradiated with a uniform dose. Thus, while a circular beam provides a "dull knife" in radiosurgery, a D-shaped beam provides a "sharp knife."

Figure 3:
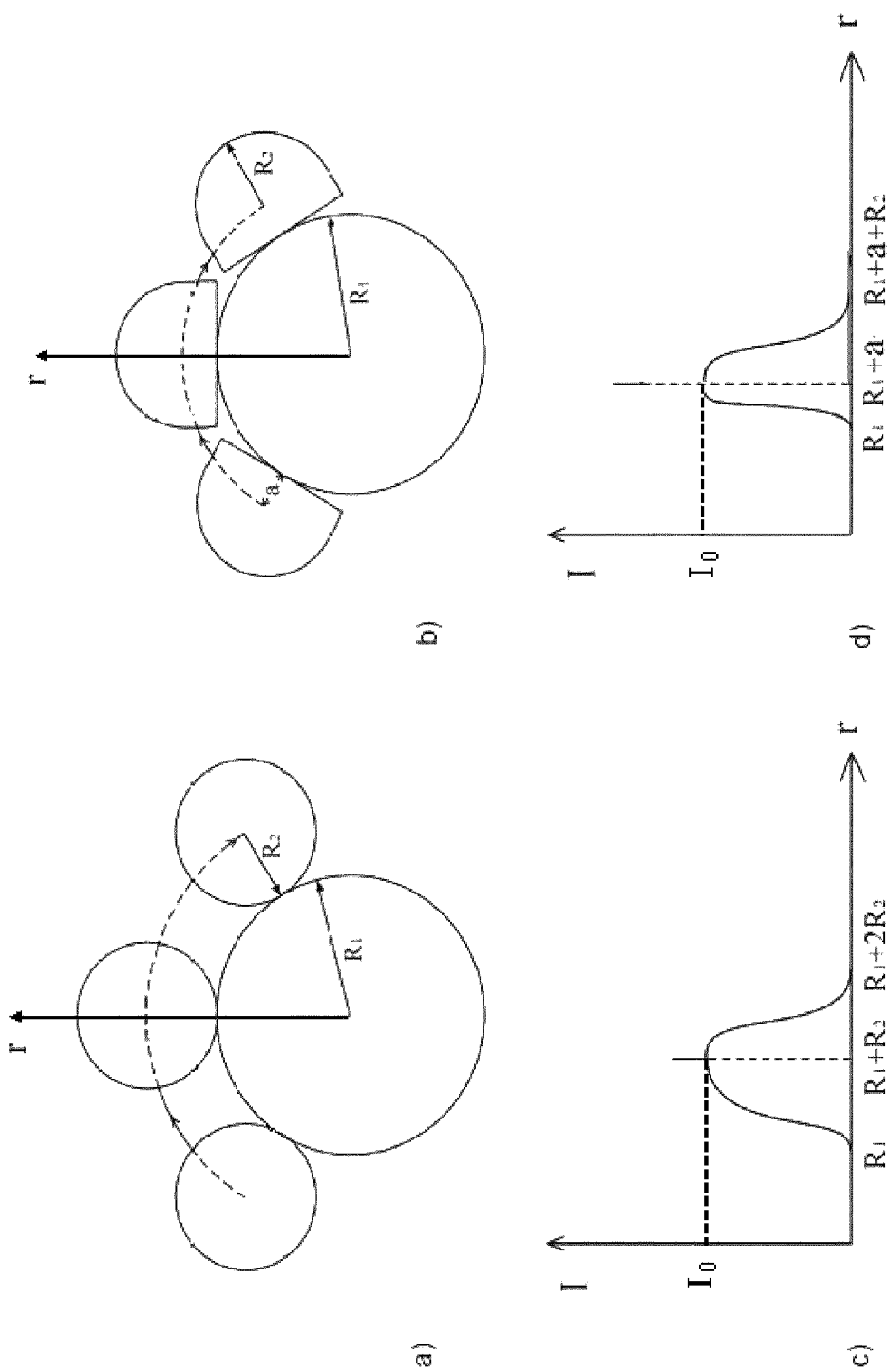
FIG. 3a is a schematic drawing of the movement of a circular radiation beam along a convex interface between a target tissue and a non-target tissue. The large circle represents such an interface and the surface of a non-target tissue. The clockwise movement of the beam in the direction of the upper arrows is represented by a series of three circles, each of which represents the circumference of the cross-section of the circular radiation beam. The convex dotted line comprising the arrows indicates the path of the central axes of the circular radiation beams. The vertical arrow (↑) labeled "r" represents the distance from the center of the non-target tissue in the radial dimension, whereas the arrow labeled "$R_1$" represents the radius of the non-target tissue and the arrow labeled "$R_2$" represents the radius of the cross-section of the circular radiation beam.
FIG. 3b is a schematic drawing of the movement of a D-shaped radiation beam along a convex interface between a target tissue and a non-target tissue. The large circle represents such an interface and the surface of a non-target tissue. The clockwise movement in the direction of the lower arrows is represented by a series of three "D" shapes, each of which represents the circumference of the cross-section of the D-shaped radiation beam. The convex dotted line comprising the arrows indicates the central axes of the D-shaped radiation beams, and "a" represents the distance between the central axis and the straight edge of the D-shaped radiation beam, which is also the width of the rectangle. The vertical arrow (↑) labeled "r" represents the distance from the center of the non-target tissue in the radial direction, whereas the arrow labeled "$R_1$" represents the radius of the non-target tissue and the arrow labeled "$R_2$" represents the distance between the central axis and the outer curved edge of the D-shaped radiation beam, which is also the radius of the half circle.
FIG. 3c is a graph of the cumulative radiation intensity (I) along the radial direction "r" of FIG. 3a, wherein the central axes of the circular radiation beams are represented by a vertical dotted line and the maximum cumulative radiation intensity is indicated by $I_0$.
FIG. 3d is a graph of the cumulative radiation intensity (I) along the radial direction "r" of FIG. 3b, wherein the central axes of the D-shaped radiation beams are represented by a vertical dotted line and the maximum cumulative radiation intensity is indicated by $I_0$.

The advantage of superimposing beams having a D-shaped cross-section is further illustrated in FIGS. 3a-3d. FIG. 3a is a schematic drawing of the movement of a circular radiation beam along a convex interface between a target tissue and a non-target tissue. The large circle represents such an interface and the surface of a non-target tissue. The clockwise movement of the beam in the direction of the upper arrows is represented by a series of three circles, each of which represents the circumference of the cross-section of the circular radiation beam. The convex dotted line comprising the arrows indicates the path of the central axes of the circular radiation beams. The vertical arrow (↑) labeled "r" represents the distance from the center of the non-target tissue in the radial direction, whereas the arrow labeled "$R_1$" represents the radius of the non-target tissue and the arrow labeled "$R_2$"

represents the radius of the cross-section of the circular radiation beam. FIG. 3b is a schematic drawing of the movement of a D-shaped radiation beam along a convex interface between a target tissue and a non-target tissue. The large circle represents such an interface and the surface of a non-target tissue. The clockwise movement in the direction of the lower arrows is represented by a series of three "D" shapes, each of which represents the circumference of the cross-section of the D-shaped radiation beam. The convex dotted line comprising the arrows indicates the central axes of the D-shaped radiation beams, and "a" represents the distance between the central axis and the straight edge of the D-shaped radiation beam, which is also the width of the rectangle. The vertical arrow (↑) labeled "r" represents the distance from the center of the non-target tissue in the radial direction, whereas the arrow labeled "$R_1$" represents the radius of the non-target tissue and the arrow labeled "$R_2$" represents the distance between the central axis and the outer curved edge of the D-shaped radiation beam, which is also the radius of the half circle. FIG. 3c is a graph of the cumulative radiation intensity (I) along the radial direction "r" of FIG. 3a, wherein the central axes of the circular radiation beams are represented by a vertical dotted line and the maximum cumulative radiation intensity is indicated by $I_0$. FIG. 3d is a graph of the cumulative radiation intensity (I) along the radial direction "r" of FIG. 3b, wherein the central axes of the D-shaped radiation beams are represented by a vertical dotted line and the maximum cumulative radiation intensity is indicated by $I_0$. If concentric curves to the surface of the non-target tissue (i.e., the circle with radius $R_1$) were drawn across the cross-section of the circular radiation beam in FIG. 3a, the curves would be intersected by the circumference of the beam (the circle with radius $R_2$). The length between the two intersection points is defined as the cord length ("c"). The intensity can be expressed as $I \approx I_o * c/(2R_2)\{(R_1+R_2)/r\}$, wherein $(R_1+R_2)/r$ is a geometric skewing factor (due to movement of the circular radiation beam along a convex interface as opposed to a flat interface). The geometric skewing factor causes the intensity profile to be asymmetric. However, by comparing FIG. 3d with FIG. 3c, it can be seen that the dose fall-off is sharp at the boundary between the target tissue and the non-target tissue when a D-shaped radiation beam is moved, whereas the dose fall-off is gentle at the boundary between the target tissue and the non-target tissue when a circular radiation beam is moved. This is why the use of circular collimators in conventional ablative radiation treatments cannot create a sharp edge along a straight line. In contrast, the use of a D-shaped collimator, in accordance with the present disclosure, can create a sharp edge along a straight line.

Figure 4:
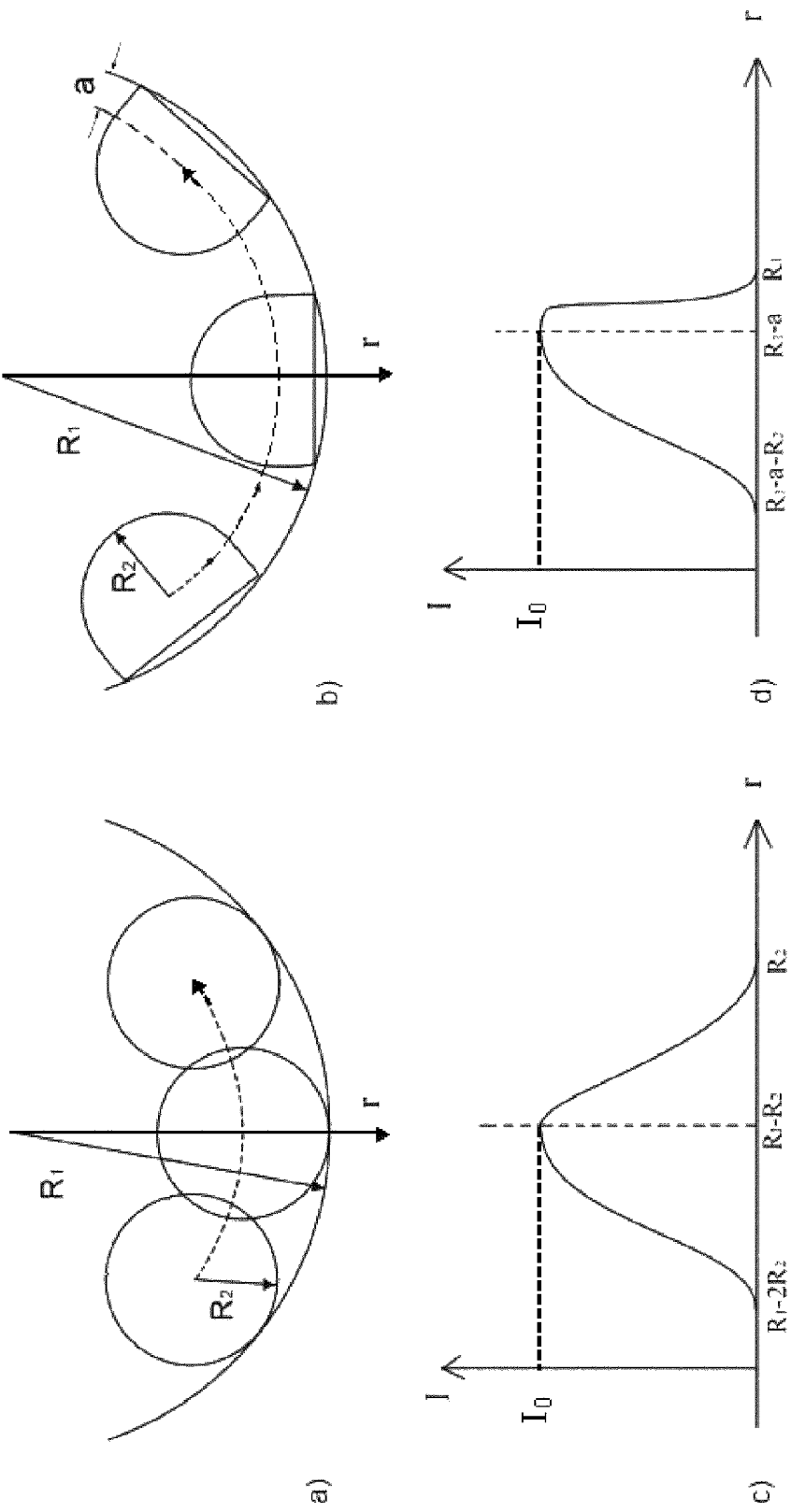
FIG. 4a is a schematic drawing of the movement of a circular radiation beam along a concave interface between a target tissue and a non-target tissue, wherein the movement is represented by a series of three overlapping circles, each of which represents the circumference of the cross-section of the circular radiation beam. The arc with radius $R_1$ represents part of the surface of the non-target tissue. The dashed concave line indicates the moving path of the central axes of the circular radiation beams. The arrow (↓) labeled "r" represents the distance from the center of the non-target tissue in the radial direction, whereas the arrow labeled "$R_2$" represents the radius of the cross-section of the circular radiation beam.
FIG. 4b is a schematic drawing of the movement of a D-shaped radiation beam along a concave interface between a target tissue and a non-target tissue, wherein the clockwise movement is represented by a series of three "D" shapes, each of which represents the circumference of the cross-section of the D-shaped radiation beam. The arc with radius $R_1$ represents part of the surface of the target tissue. The dashed concave line comprising the arrows indicates the moving path of the central axes of the D-shaped radiation beams, and "a" is the width of the rectangular portion of the cross-section of the D-shaped radiation beam. The arrow (↓) labeled "r" represents the distance from the center of the target tissue in the radial direction, whereas the arrow labeled "$R_2$" represents the distance between the central axis and the center of the outer curved edge of the D-shaped radiation beam, which is also the radius of the half circle.
FIG. 4c is a graph of the cumulative radiation intensity (I) along the radial direction "r" of FIG. 4a, wherein the central axes of the circular radiation beams are represented by a vertical dotted line and the maximum cumulative radiation intensity is indicated by $I_0$.
FIG. 4d is a graph of the cumulative radiation intensity (I) along the radial direction "r" of FIG. 4b, wherein the central axes of the D-shaped radiation beams are represented by a vertical dotted line and the maximum cumulative radiation intensity is indicated by $I_0$.

The advantage of superimposing beams having a D-shaped cross-section is still further illustrated in FIGS. 4a-4d. FIG. 4a is a schematic drawing of the movement of a circular radiation beam along a concave interface between a target tissue and a non-target tissue, wherein the movement is represented by a series of three overlapping circles, each of which represents the circumference of the cross-section of the circular radiation beam. The arc with radius $R_1$ represents part of the surface of the target tissue. The dashed concave line indicates the moving path of the central axes of the circular radiation beams. The arrow (↓) labeled "r" represents the distance from the center of the non-target tissue in the radial direction, whereas the arrow labeled "$R_2$" represents the radius of the cross-section of the circular radiation beam. FIG. 4b is a schematic drawing of the movement of a D-shaped radiation beam along a concave interface between a target tissue and a non-target tissue, wherein the clockwise movement is represented by a series of three "D" shapes, each of which represents the circumference of the cross-section of the D-shaped radiation beam. The arc with radius $R_1$ represents part of the surface of the target tissue. The dashed concave line comprising the arrows indicates the moving path of the central axes of the D-shaped radiation beams, and "a" is the width of the rectangular portion of the cross-section of the D-shaped radiation beam. The arrow (↓) labeled "r" represents the distance from the center of the target tissue in the radial direction, whereas the arrow labeled "$R_2$" represents the distance between the central axis and the center of the outer curved edge of the D-shaped radiation beam, which is also the radius of the half circle. FIG. 4c is a graph of the cumulative radiation intensity (I) along the radial direction "r" of FIG. 4a, wherein the central axes of the cylindrical radiation beams are represented by a vertical dotted line, and the maximum cumulative radiation intensity is indicated by $I_0$. FIG. 4d is a graph of the cumulative radiation intensity (I) along the radial direction "r" of FIG. 4b, wherein the central axes of the D-shaped radiation beams are represented by a vertical dotted line and the maximum cumulative radiation intensity is indicated by $I_0$. If concentric curves to the surface of the target (i.e., the large arc with radius $R_1$) were drawn across the cross-section of the circular radiation beam, the curves would be intersected by the circumference of the beam (the circle with radius $R_2$). The length between the two intersection points is defined as the cord length ("c"). The intensity can be expressed as $I=I_o*c/(2R_2)\{r/(R_1-R_2)\}$, wherein $(r/R_1-R_2)$ is a geometric skewing factor (due to movement of the circular beam along a concave interface as opposed to a flat interface). The geometric skewing factor causes the intensity profile to be asymmetric. Here, again, however, by comparing FIG. 4d with FIG. 4c, it can be seen that the dose fall-off is sharp at the target boundary when a D-shaped radiation beam is moved, whereas the dose fall-off is gentle at the target boundary when a circular radiation beam is moved.

Arcs or many beams are often used to create a high dose volume. For a complete 360-degree arc, the high-dose volume created with circular beams is a sphere. Moving such a sphere to form a flat surface (i.e., interface) separating a target tissue from a non-target tissue is even harder. The radiation intensity along the line perpendicular to the interface is proportional to the area of the intersection of a plane parallel to the interface and the sphere, i.e., $I=I_o*c^2/(2R)^2$, where R is the radius of the beams, causing an even gentler fall-off than moving a circular beam along a line. With D-shaped beams, a complete arc produces a dome-shaped, high-dose volume with a flat bottom and a hemispherical top. The flat bottom can shape a flat surface (i.e., interface) separating a target tissue from a non-target tissue, whereas the hemispherical top can shape a round surface.

Figure 5A:
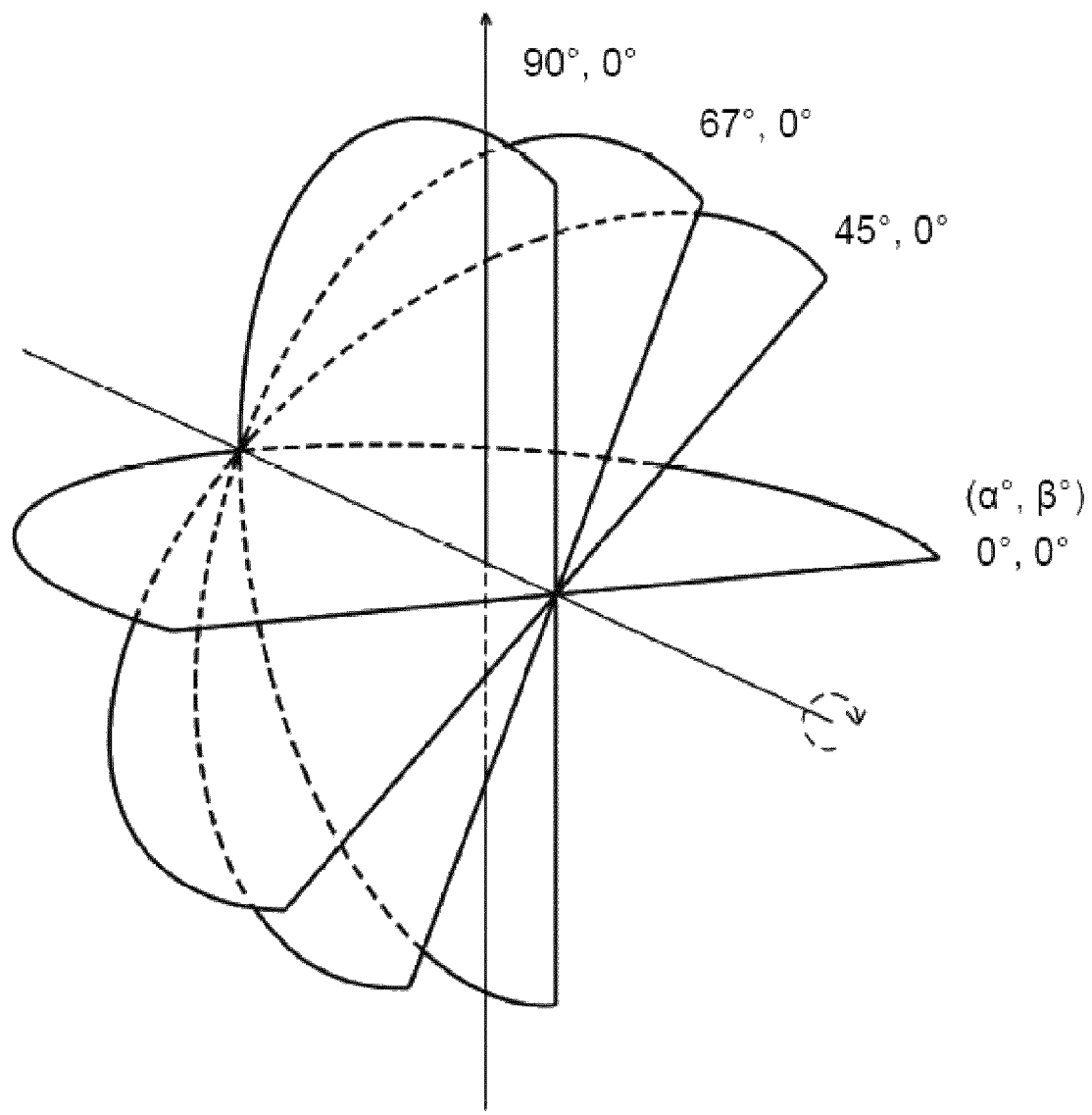
FIG. 5a is a schematic drawing illustrating the projection outline of multiple intersecting D-shaped beams at different beam angles (α) and a fixed collimator angle (β=0), wherein the vertical arrow (↑) represents the central axis of a 0° beam and the other arrow represents the axis of rotation, and wherein the beams can be created with multiple sources of radiation or a single arcing beam.
Figure 5B:
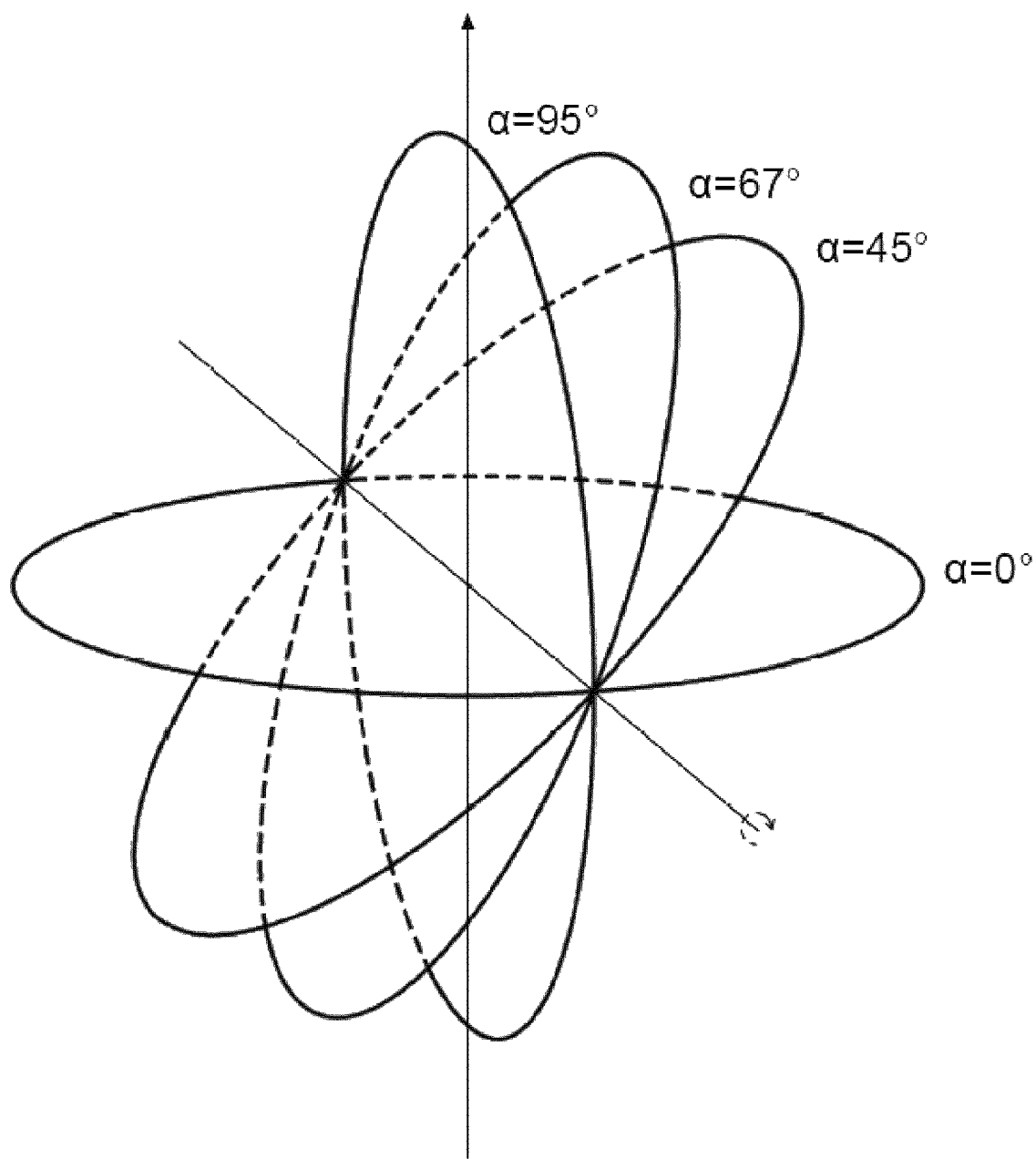
FIG. 5b is a schematic drawing illustrating the projection outline of multiple intersecting cylindrical beams at different beam angles (α) and a fixed collimator angle (β=0), wherein the vertical arrow (↑) represents the central axis of a 0° beam and the other arrow represents the axis of rotation, and wherein the beams can be created with multiple sources of radiation or a single arcing beam.

More generally, multiple coplanar beams of different orientations are used to create a high-dose gradient at the boundary of the target tissue and the non-target tissue. This is illustrated in FIG. 5a, which is a schematic drawing illustrating the projection outline of multiple intersecting D-shaped beams at different beam angles (α) and a fixed collimator angle (β=0), wherein the vertical arrow (↑) represents the central axis of a 0° beam and the other arrow represents the axis of rotation, and wherein the beams can be created with multiple sources of radiation or a single arcing beam. The flat edges of all of the D-shaped beams are coplanar, such that the axes of all beams intersect at the same point. The flat edges of the D-shaped beams form a plane, one side of which is always shielded and the other side of which has a high radiation intensity due to the overlapping of multiple beams. The curved side of the D forms a rounded edge of the high dose volume. Depending on the interface surface the beams try to shape, D-shaped beams have the flexibility of using different shapes of edges to match that of the interface. In contrast, FIG. 5b is a schematic drawing illustrating the projection outline of multiple intersecting cylindrical beams at different beam angles ($\alpha$) and a fixed collimator angle ($\beta$=0), wherein the vertical arrow ($\uparrow$) represents the central axis of a 0° beam and the other arrow represents the axis of rotation, and wherein the beams can be created with multiple sources of radiation or a single arcing beam. There is no flat edge as with the D-shaped beams.

Figure 6A:
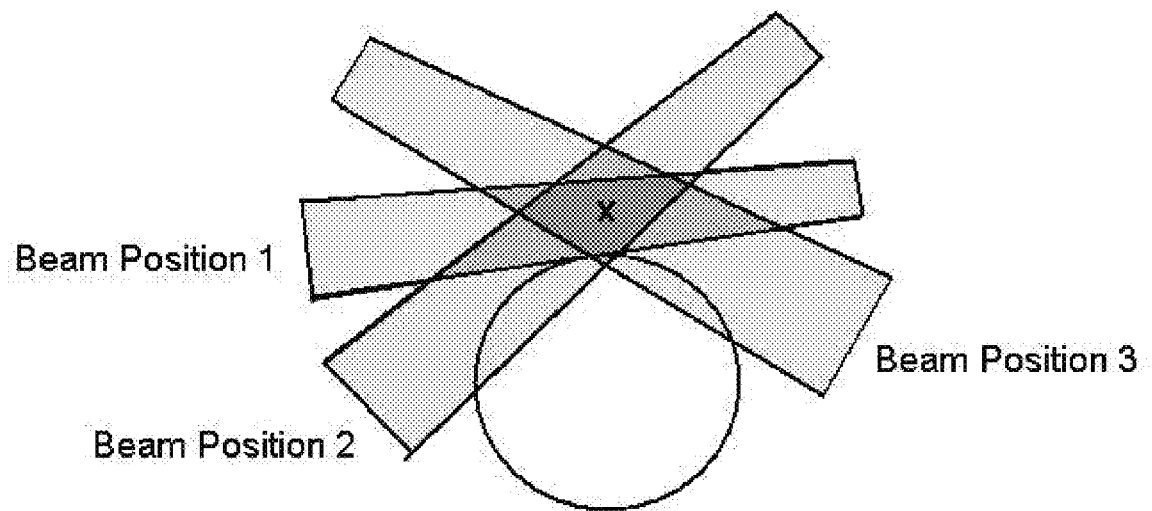
FIG. 6a is a schematic drawing illustrating the conventional rotation of a beam (Beam Positions 1, 2, and 3) around a fixed point or isocenter ("x"), which is adjacent to a non-target tissue (delineated by the circle).
Figure 6B:
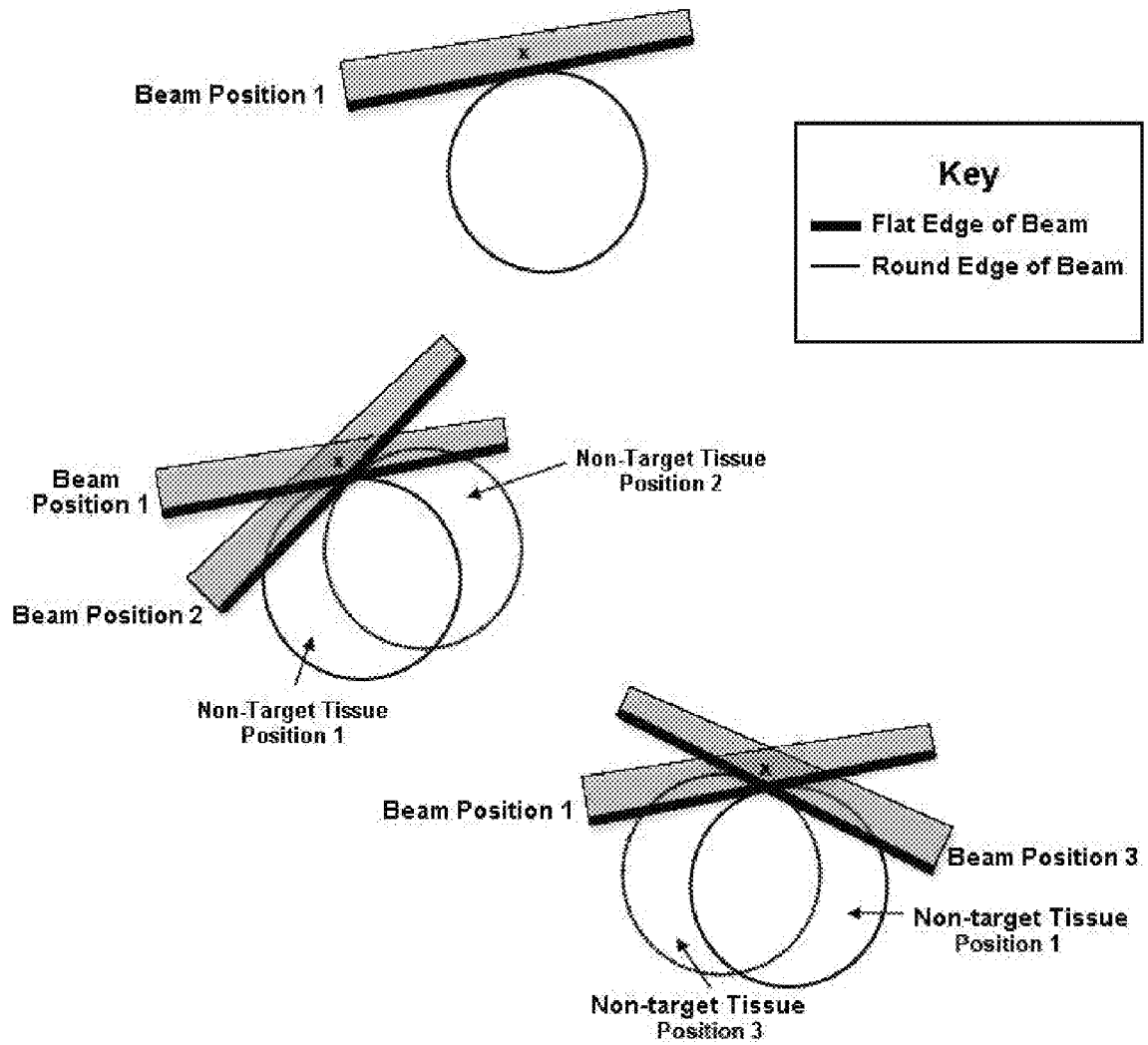
FIG. 6b is a schematic drawing illustrating that coordination of rotation of a beam with a D-shaped cross-section (Beam Positions 1, 2, and 3) around a fixed point or isocenter ("x"), which is adjacent to a non-target tissue (delineated by the circle), with movement of a patient (represented by the Non-Target Tissue Positions 1, 2 and 3).
Figure 7:
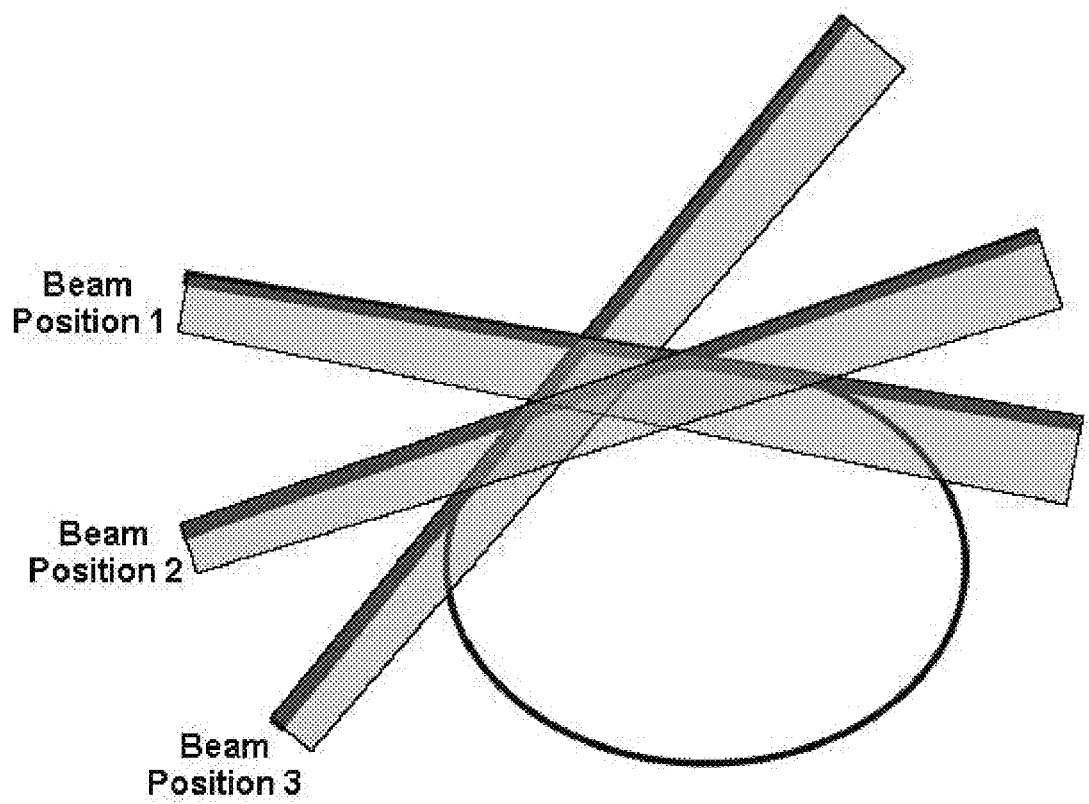
FIG. 7 is a schematic drawing illustrating that coordination of rotation of a beam (Beam Positions 1, 2, and 3) with movement of a patient, such that each beam position is associated with a different patient position, shapes a high dose surface covering the target tissue (represented by the large oval).
Figure 7:
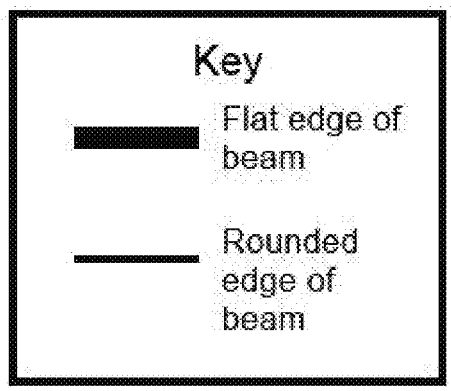

Conventional radiation treatments have been implemented by only rotating the radiation beam around a fixed point in the patient. This is illustrated in FIG. 6a, which is a schematic drawing illustrating the conventional rotation of a beam (Beam Positions 1, 2, and 3) around a fixed point or isocenter ("x"), which is adjacent to a non-target tissue (delineated by the circle). As shown in FIG. 6a, optimal sparing of non-target tissue is not possible with this arrangement when fixed collimators are used (as often are) in radiosurgery. In accordance with the method of the present disclosure, the motion of the patient positioning system is coordinated with the rotation of a radiation beam. When the radiation beam is D-shaped, the straight edge of the D-shaped beam is kept tangential to the boundary of the high-dose volume, thereby maintaining a sharp dose fall-off. This is illustrated in FIG. 6b, which is a schematic drawing illustrating that coordination of rotation of a beam with a D-shaped cross-section (Beam Positions 1, 2, and 3) around a fixed point or isocenter ("x"), which is adjacent to a non-target tissue (delineated by the circle), with movement of a patient (represented by the Non-Target Tissue Positions 1, 2 and 3). A sharp dose drop-off results at the interface between the target tissue and the non-target tissue, thereby protecting the non-target tissue without underdosing the target tissue. As shown in FIG. 6b, when the beam is in position 1, the non-target tissue is in position 1. When the beam is in position 2, the patient is moved such that the non-target tissue is moved from position 1 to position 2. Likewise, when irradiating the target tissue with the beam in position 3, the non-target tissue is moved to position 3. This arrangement allows the sparing of non-target tissue within and/or adjacent to (e.g., surrounding) the target tissue. As shown in FIG. 7, which is a schematic drawing illustrating that coordination of rotation of a beam (Beam Positions 1, 2, and 3) with movement of a patient, such that each beam position is associated with a different patient position, a high dose surface covering the target tissue (represented by the large oval) can be shaped.

Figure 12:
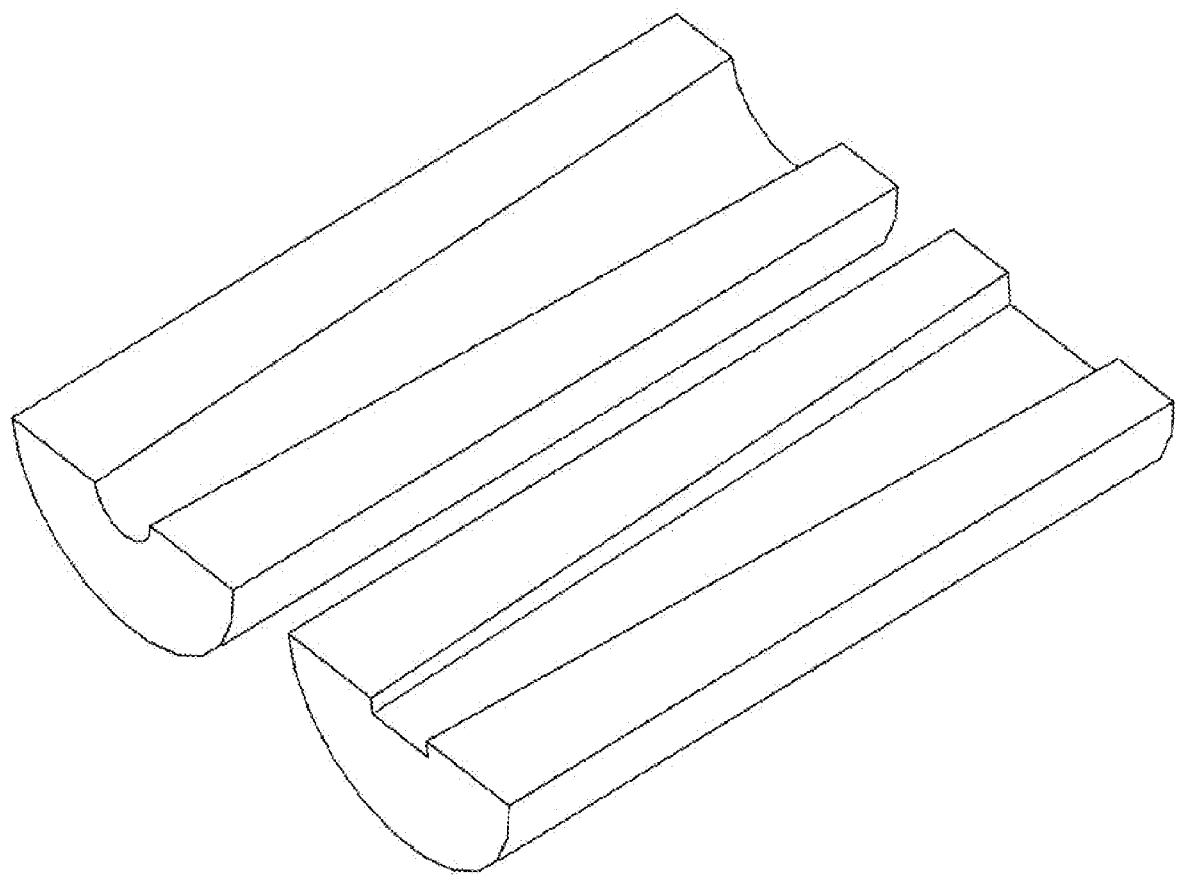
FIG. 12 shows half of a circular (cross-section) collimator with a cone-shaped tunnel and half of a rectangular (cross-section) collimator with a pyramid-shaped tunnel having the same divergence as the half of a circular (cross-section) collimator with a cone-shaped tunnel. The two halves can be joined to create a D-shaped collimator in accordance with the present disclosure.

In view of the above method, also provided is a collimator, in particular a collimator with a fixed opening and divergence, which (a) shapes a beam of radiation to have a D-shaped cross-section, (b) maintains the central axis of the beam of radiation on or adjacent to the straight edge of the D-shaped cross-section of the beam of radiation, and (c) can fully rotate the beam of radiation in either direction about the beam axis, such that the straight edge of the D-shaped cross-section of the beam of radiation can face any direction. Such a collimator can be made by joining half of a circular collimator with a conical-shaped tunnel with half of a rectangular collimator with a pyramid-shaped tunnel. The two halves should have the same divergence. FIG. 12 shows half of a circular (cross-section) collimator with a cone-shaped tunnel and half of a rectangular (cross-section) collimator with a pyramid-shaped tunnel having the same divergence as the half of a circular (cross-section) collimator with a cone-shaped tunnel. The two halves can be joined to create a D-shaped collimator. Such collimators should be made from a high density material, preferably tungsten alloy. Different methods can be used for joining the two halves, such as, for example, welding, screw-tightening, clamping, and the like. Once they are joined together, the cross-section of such a collimator at every height level would show a D-shaped opening, formed by a half-circle and a narrow rectangle. The movement of the collimator can be coordinated with movement of the patient support system and rotation of the beam of radiation. As illustrated in FIGS. 3a-3d and 4a-4d, such a collimator can create a sharp dose gradient along a line as well as a "cold" hole surrounded by "hot" regions. This ability is analogous to a sharp knife, which can sculpt an intricate high-dose volume of complex shape. The collimator can rotate 360°, such that the flattened edge of the "D" can face all directions. By tangentially moving the straight edge along the direction of a linear interface, for example, such as an interface between a target tissue and a non-target tissue, the maximum dose is not moved away from the edge, thereby maintaining a sharp dose drop-off when multiple beams are overlapped or abutted, as is often the case in modern radiation treatments. The reason for this is that the straight edge is kept as close as possible to the axis of the radiation beam, which is where the beam of radiation is straight, thereby minimizing beam divergence. In contrast, movement of a circle along a linear interface results in the maximum dose being delivered at the center of the circle, which is at a distance away from the edge equal in length to the radius of the circle. When trying to preserve a non-target tissue within a target tissue, such as a urethra within a cancerous prostate, the straight edge of the "D" is kept tangential to the outer surface of the non-target tissue, i.e., the urethra in this example, such that the non-target tissue is always shielded and the beam is kept inside the target tissue, i.e., in the cancerous prostate in this example.

Accordingly, a system for irradiating a target tissue in a patient is also provided. The system comprises (i) a patient support system, which comprises (a) a table or a couch, either of which is optionally padded, (b) one, two or three motors, each of which drives movement of the table or the couch in the direction of a separate axis, (c) optionally, a base, in which case the one or more motors can be housed in the base, and (d) a computerized control system, which can control the movement of the patient support system; (ii) at least one rotatable source of a beam of radiation, wherein each source of a rotatable beam of radiation can be rotated around a target tissue in a patient positioned on the patient support system; (iii) at least one collimator, wherein each collimator is operably aligned with one rotatable source of a beam of radiation; and (iv) a central control unit, which can execute a patient treatment plan including rotation of at least one rotatable source of a beam of radiation relative to a target tissue in a patient positioned on a patient support system, rotation of the at least one rotatable source of a beam of radiation, and movement of a patient support system. Preferably, the at least one collimator (a) shapes the beam of radiation to have a D-shaped cross-section, (b) maintains the central axis of the beam of radiation on or adjacent to the straight edge of the D-shaped cross-section of the beam of radiation, and (c) can fully rotate the D-shaped cross-section of the beam of radiation in either direction, such that the straight edge of the D-shaped cross-section of the beam of radiation can face any direction Also provided is a computer optimization method to plan dynamic radiation sculpting in accordance with the present disclosure. As with line arts, where the tangent lines to a two-dimensional or a three-dimensional surface can be determined analytically or numerically, the beam lines can be determined once the volume (and its surface) of the target tissue and the adjacent or internal non-target tissue(s) are known. When a radiation beam can traverse every point in the target from every direction, the number of parameters to optimize is enormous. Thus, points on the surface of the target tissue and, if present, its enclosed non-target tissue and other points inside the target tissue are treated separately. The surface of the target tissue and any non-target tissue in and/or adjacent to the target tissue are modeled as a connection of grid points in the computer. For each point on the surface of the target tissue, there are two unique beams from two opposing directions that can be tangential to the surface and with the straight edge of the "D" facing the surface. When the central axis of the beam is kept stationary such that the beam is tangential to the surface of the target tissue, it is easy to compute the unique corresponding coordinates of the patient support system for each of the beams. Because the beam parameters, including orientation, collimator angle, and the coordinates of the patient support system are relatively fixed for the surface points, the planning system can determine the control parameters for these points in a deterministic fashion. Inside the target tissue and in regions away from the surfaces, there is no restriction as to the beam direction, collimator angle, or where the straight edge of the "D" should intersect. The planning system has more freedom to determine these parameters as needed for creating the desired dose distribution.

Because the radiation beam is straight at the beam axis and diverges away from the beam axis, in order to keep the beam edge sharp, the straight edge of the "D"-shaped collimator should stay on or adjacent to the central axis of the beam. One method of describing such a set of lines that define a curve or curved surface is using Bezier curves that are defined by a set of parametric equations. The basic Bezier curve is defined by four control points. However, this method can easily be extended to curves of higher degree. The parametric equation describing a Bezier curve is:

$$b^n(t) = \sum_{i=0}^{n} b_i \binom{n}{i} t^i (1-t)^{n-i}$$

where $b^0$ is the first point and n is the number of points.

Figure 8:
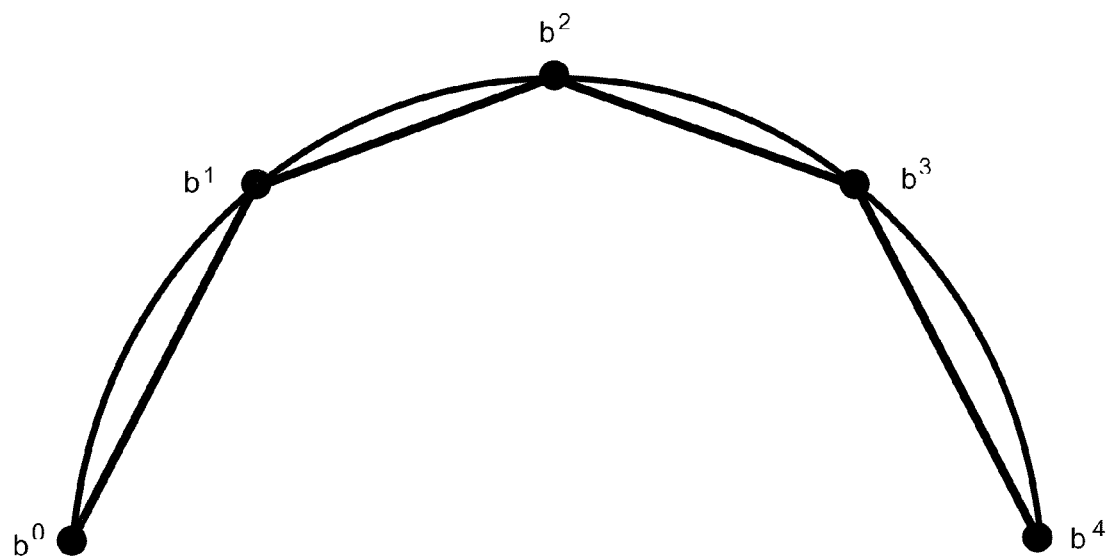
FIG. 8 is a schematic drawing illustrating the parametric points b″(t) defining a hull at a convex surface, wherein "b" represents the point, "n" represents the index number of points, and "t" represents time.

A second degree Bezier function describes a curve, as illustrated in FIG. 8. FIG. 8 is a schematic drawing illustrating the parametric points $b''(t)$ defining a hull at a convex surface, wherein "b" represents the point, "n" represents the index number of points, and "t" represents time. The time interval between two successive points is the irradiation time, which is optimized to create the desired dose distribution. In each case the parametric lines define a convex hull surrounding the curve but by definition not crossing into the function. A third degree function describing a surface and a fourth degree function can be used to model smooth motion.

Bezier functions are often used to describe computer-generated surfaces. These functions can be used to define equidistant points on the surface. A simple strategy to define a sculpted path is to determine the tangent to these points with a margin normal to the tangent.

Figure 9:
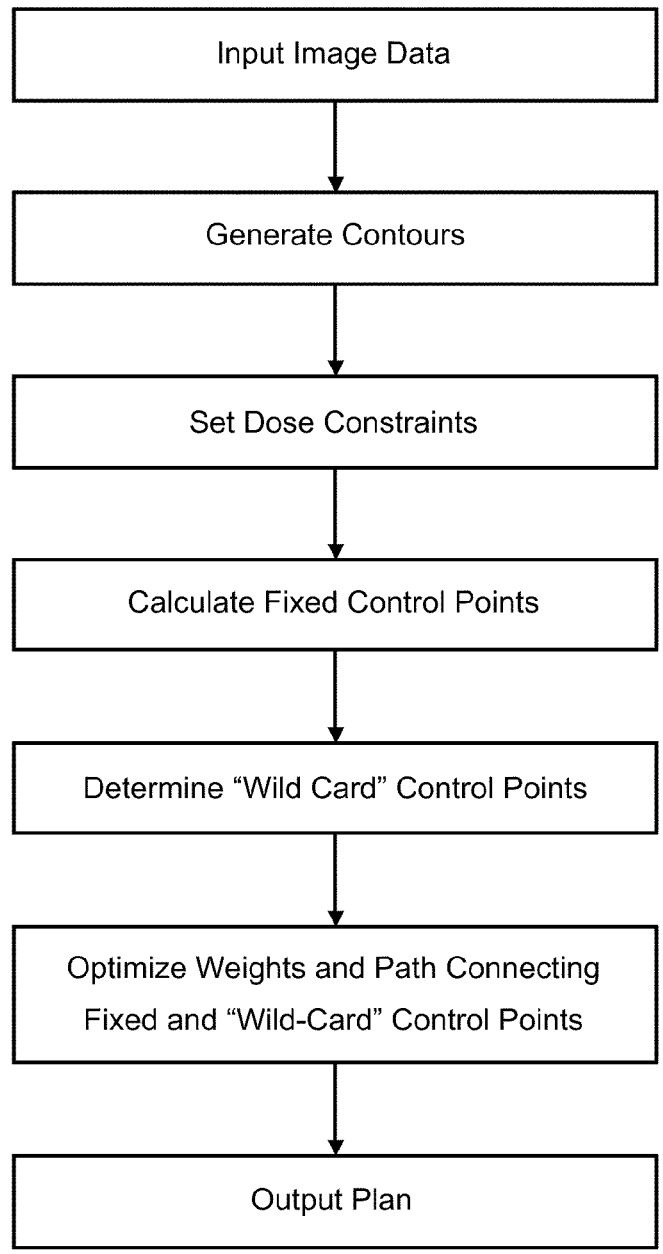
FIG. 9 is a flowchart setting forth key steps of a treatment plan for dynamic sculpting in accordance with the present disclosure.

FIG. 9 is a flowchart setting forth key steps of a treatment plan for dynamic sculpting in accordance with the present disclosure. The first task of planning the dynamic radiation sculpting is to find all such beams. The corresponding Bezier surface description is computed for the surface of the target tissue and the non-target tissue in and/or adjacent to the target tissue. A set of equidistant points induced by these Bezier surfaces are then used to determine the "D"-shaped beams, which are tangential to the surface. Each of these beams forms a control point, which defines the radiation beam angle, the orientation of the "D" collimator, and the patient support system coordinates.

Figure 10:
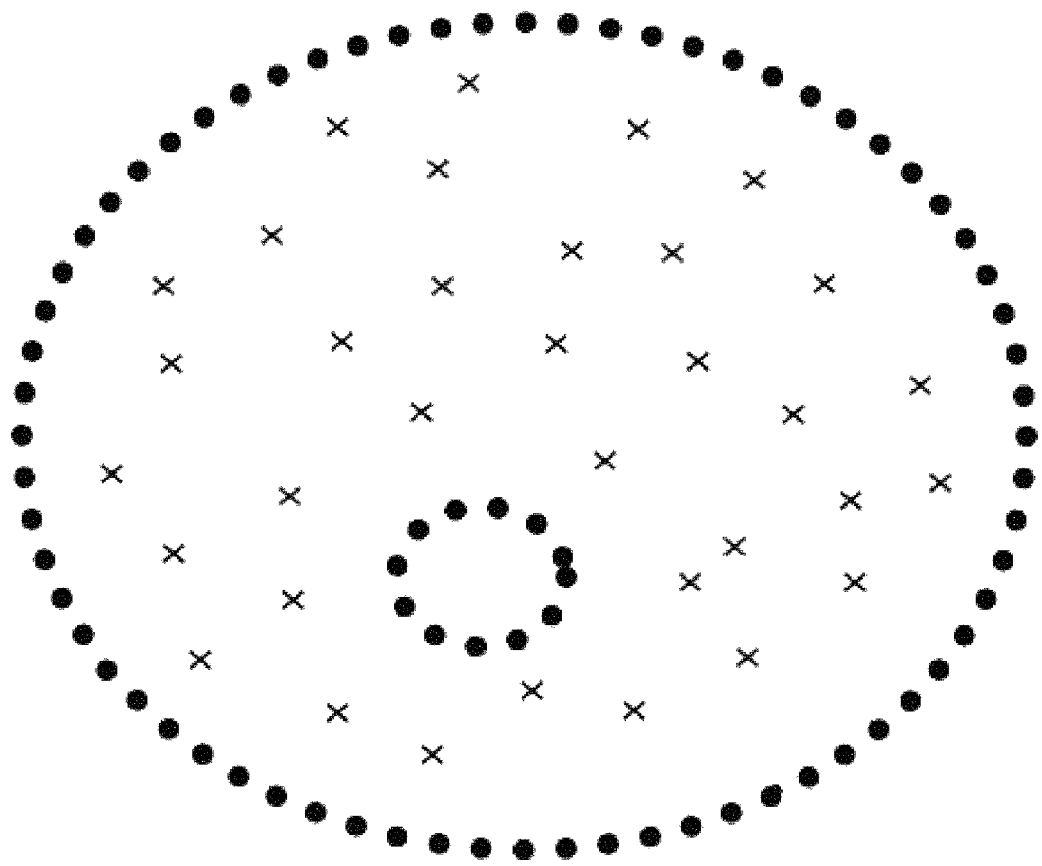
FIG. 10 is a schematic drawing illustrating the concept of using fixed (•) and "wildcard" (×) points to determine treatment delivery. In this example, fixed points are placed at the surface of the target tissue (represented by the large oval) and at the surface of a non-target tissue (represented by the small circle) within the target tissue.

The points inside the target are "wild cards." A beam needs to pass these points, but it can come from any direction. For a given beam direction, the coordinates of the patient support system also have some freedom. FIG. 10 is a schematic drawing illustrating the concept of using fixed (•) and "wild card" (×) points to determine treatment delivery. In this example, fixed points are placed at the surface of the target tissue (represented by the large oval) and at the surface of a non-target tissue (represented by the small circle) within the target tissue.

The second task of planning the dynamic radiation sculpting is to find the motion path by connecting the control points. Motion constraints for the beam angle and movement of the patient support system are applied to connect all of the control points. Optimization algorithms, such as the algorithm for solving the "traveling salesman problem" in three-dimensional Euclidean space, is used to minimize the motion and to ensure that all control points are visited with minimal repeating of a traveled path. The "wild card" points inside the target can be used to connect the surface points when necessary. The weightings of each beam are optimized so that the dose of radiation is uniform within the surface boundaries. This optimization problem can be modeled as a constrained nonlinear programming and can be solved by using techniques such as simulated annealing.

After sculpting the surfaces of the target tissue and non-target tissue(s), the most difficult task is completed. The optimization system then checks the resulting radiation dose distribution against the desired dose distribution. More control points can be added to make up the difference between the desired dose distribution and the delivered dose distribution. The motion path computed in the previous step is then adjusted accordingly.

So far, the beam with a "D"-shaped cross section is regarded as emitted from one radiation source. It also can be from two or more sources. The use of two or more sources allows the dose rate to be shared by all of the sources. When using accelerated electrons to generate the radiation beams, this allows the tube current of each source to be smaller. When such sources are radioactive materials, the use of two or more sources also allows each of the sources to be smaller, resulting in a narrower penumbra and a sharper dose fall off at the edge of the beam.

In view of the above, also provided is a method of planning irradiation of a target tissue in a patient with a system for irradiating a target tissue in a patient. The method comprises: (i) determining the volume and the surface contour of the target tissue to be irradiated and, if present, the volume and the surface contour of a non-target tissue located wholly within the target tissue and/or the surface contour and, optionally, the volume of a non-target tissue located partially within the target tissue, (ii) setting the radiation dose to be delivered to the target tissue and limiting the radiation dose to the non-target tissue, (iii) assigning control points to the surface contours identified in (i), (iv) determining the angle of the beam of radiation, the orientation of the collimator, and the position of the patient support system at each control point, (v) assigning "wild card" points within the volume of the target tissue with the proviso that a "wild card" point is not assigned within the volume of any non-target tissue that is located wholly or partially within the target tissue, (vi) determining the path of motion when all control points and, optionally, one or more "wild card" points, are connected and optimizing the weighting of each beam of radiation so as to provide a uniform dose of radiation within the target tissue and a sharp drop-off away from the boundary between the target tissue and any non-target tissue, and (vii) checking the resulting radiation dose distribution against a desired radiation dose distribution and adjusting the path of motion and the weightings of control points accordingly and, if needed, adding more control points. By "weighting" is meant the amount of time spent at a control point. When more time is to be spent at a control point, the control point has more weighting. When less time is to be spent at a control point, the control point has less weighting. By "sharp drop-off" is meant to have a high dose gradient where a large change in the radiation dose occurs over a short distance. For example, a change in the radiation dose from 90%, for example, to 50%, for example, over a distance of a few millimeters, such as 5 mm or less, is considered to be a sharp drop-off. The radiation dose to the non-target tissue can be limited by establishing maximum dose, mean dose, and doses allowed to certain percentages of the volume of the non-target tissue, for example.

EXAMPLE

The following example serves to illustrate the present disclosure. The example is not intended to limit the scope of the claimed invention in any way.

Figure 11A:
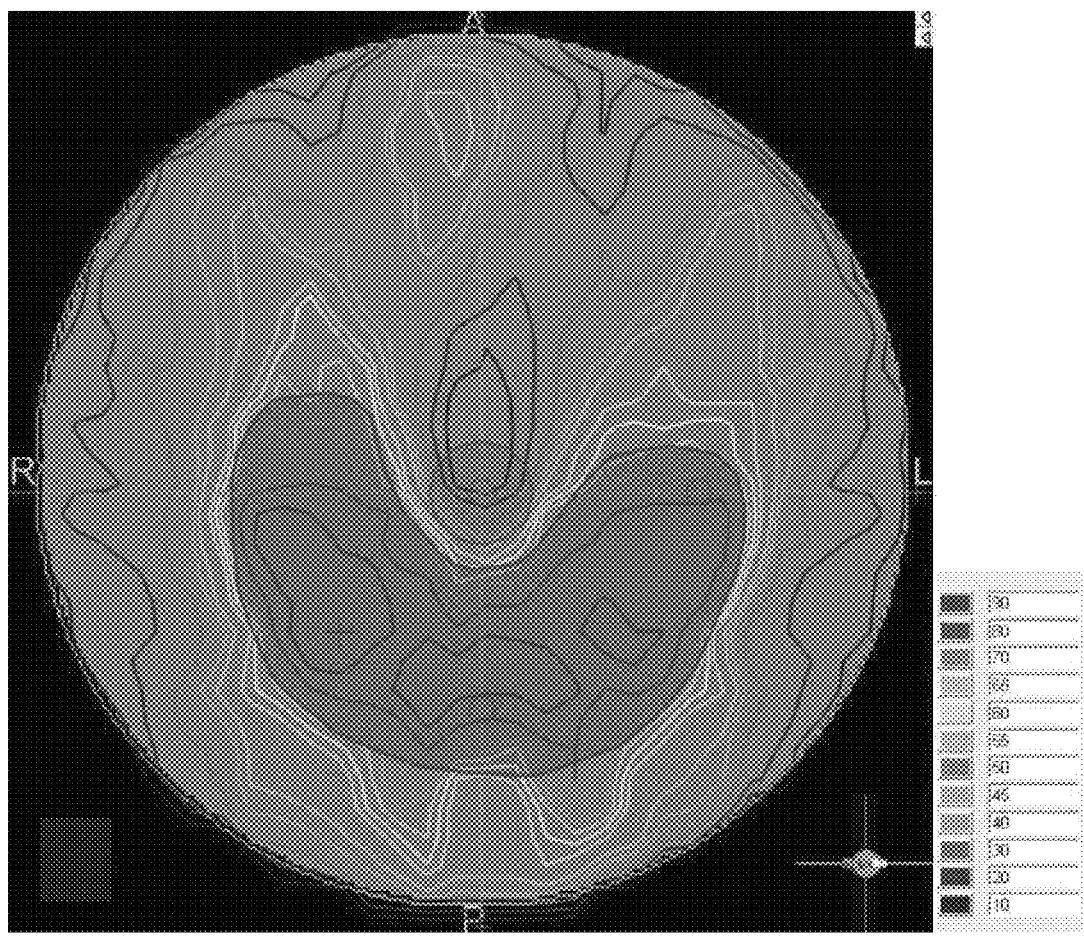
FIG. 11a shows the isodose distribution resulting from a computer-optimized treatment plan using beams of D-shaped cross-section for a hypothetical problem.
Figure 11B:
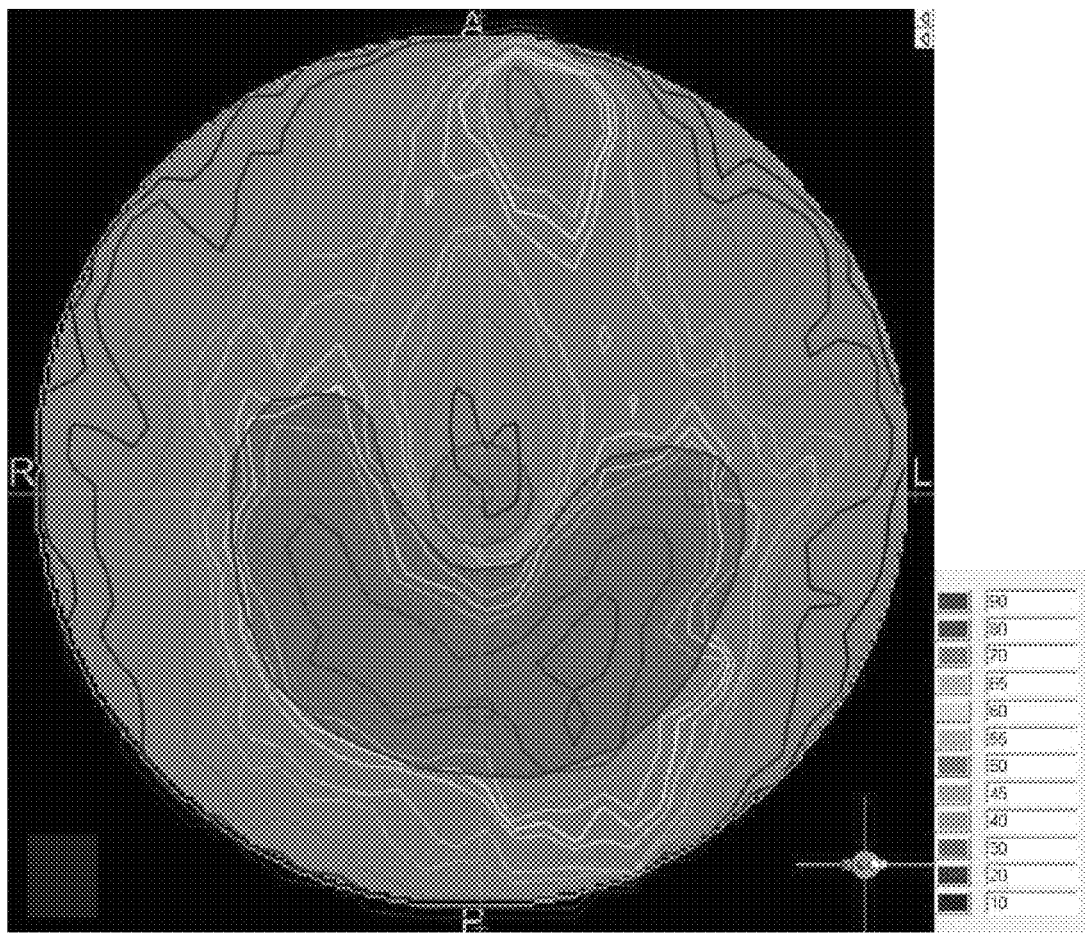
FIG. 11b shows the isodose distribution resulting from a computer-optimized treatment plan using beams of circular cross-section for a hypothetical problem.

This example describes a simulation of the method in accordance with the present disclosure. For the simulation, a target shaped as half of a doughnut with a cylindrical "critical structure" located at the center hole of the doughnut is placed inside a larger cylinder of uniform density resembling the torso of the human body. The goal is to deliver as high a dose as possible to the entire target, while minimizing the dose to the critical structure and other normal tissues. FIGS. 11a and 11b show the isodose distributions resulting from computer-optimized treatment plans using beams collimated with a D-shaped collimator (FIG. 11a) and beams collimated with a traditional circular collimator. When the D-shaped collimators are used (FIG. 11a), a higher dose gradient is created at the boundary of the target tissue, as indicated by the closely spaced isodose lines around the target boundary. More than 95% of the target is covered by the 70% isodose line. The "hot spot" within the normal tissue anterior to the target and the critical structure receive 50% of the maximum dose. The critical structure receives the highest dose of 40%. When the traditional circular beams are used (FIG. 11b), 95% of the target is covered by the 55% isodose line. The "hot spot" within the normal tissue anterior to the target and the critical structure receive 90% of the maximum dose. The critical structure receives the highest dose of 45% of the maximum dose.

In radiation treatments, the target must receive the prescribed dose. If both plans are to deliver the same prescription dose, the critical structure would receive 57% and 82% of the prescription dose resulting from the use of D-shaped beams and circular beams, respectively. The hot spot at the anterior region inside the torso would be 71% and 164% of the prescription dose resulting from the use of D-shaped beams and circular beams, respectively. This example illustrates the significant advantage of using D-shaped collimators in creating sharp dose gradients.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation (s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" include one or more methods and/or steps of the type described herein and/or apparent to those ordinarily skilled in the art upon reading the disclosure.

The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of irradiating a target tissue in a patient, which method comprises:

positioning the patient on a patient support system so that the target tissue in the patient is within irradiating distance of multiple beams of radiation, wherein (a) each beam, which is from a different source or a single arcing source, is from a different direction and has a central axis, (b) the central axes of the multiple beams are focused on a fixed point in the target tissue, and (c) each beam rotates around its own central axis and around the fixed point of focus, and continuously moving the patient support system relative to the fixed point of focus of the multiple beams of radiation and, coordinately with movement of the patient support system, continuously rotating at least one beam of radiation around the fixed point of focus in the target tissue, which comprises and/or is adjacent to a non-target tissue, so that the fixed point of focus is constantly moving within the target tissue, while simultaneously and/or sequentially irradiating the target tissue, whereupon the target tissue in the patient is irradiated in a pattern created by the coordinated continuous movement of the patient support system and the continuous rotation of at least one beam of radiation around the fixed point of focus in the target tissue.

2. The method of claim 1, wherein the beam of radiation has a D-shaped cross-section.

3. The method of claim 2, wherein the straight edge of the D-shaped cross-section of the beam of radiation is placed tangentially to the boundary of the target tissue and the non-target tissue, as the beam of radiation is rotated.

4. A collimator, which (i) shapes a beam of radiation to have a D-shaped cross-section, (ii) maintains the central axis of the beam of radiation on or adjacent to the straight edge of the D-shaped cross-section of the beam of radiation, and (iii) fully rotates the beam of radiation in either direction about the beam axis during irradiation, such that the straight edge of the D-shaped cross-section of the beam of radiation faces any direction during irradiation.

5. A method of making the collimator of claim 4, which method comprises joining half of a circular (cross-section) collimator with a cone-shaped tunnel with half of a rectangular (cross-section) collimator with a pyramid-shaped tunnel, where the circular and the rectangular collimators have the same divergence, whereupon the collimator is made.

6. A system for irradiating a target tissue in a patient comprising:
   (i) a patient support system, which comprises (a) a table or a couch, either of which is optionally padded, (b) one or more motors, each of which drives movement of the table or the couch in the direction of a separate axis, (c) optionally, a base, in which case the one or more motors are housed in the base, and (d) a computerized control system, which controls the continuous movement of the patient support system;
   (ii) multiple beams of radiation, wherein (a) each beam, which is from a different source or a single arcing source, is from a different direction and has a central axis, (b) the central axes of the multiple beams are focused on a fixed point in the target tissue, and (c) each beam rotates around its own central axis and around the fixed point of focus;
   (iii) at least one collimator, wherein each collimator is operably aligned with one rotatable source of a beam of radiation; and
   (iv) a central control unit, which executes a patient treatment plan including coordinating continuous rotation of at least one beam of radiation around its own central axis, continuous rotation of at least one beam of radiation around the fixed point of focus, and continuous movement of a patient support system relative to the fixed point of focus of the multiple beams of radiation.

7. The system of claim 6, wherein the at least one collimator (a) shapes the beam of radiation to have a D-shaped cross-section, (b) maintains the central axis of the beam of radiation on or adjacent to the straight edge of the D-shaped cross-section of the beam of radiation, and (c) fully rotates the D-shaped cross-section of the beam of radiation in either direction, such that the straight edge of the D-shaped cross-section of the beam of radiation faces any direction during irradiation.

8. A method of planning irradiation of a target tissue in a patient with the system of claim 6, which method comprises:
   (i) determining the volume and the surface contour of the target tissue to be irradiated and, if present, the volume and the surface contour of a non-target tissue located wholly within the target tissue and/or the surface contour and, optionally, the volume of a non-target tissue located partially within the target tissue,
   (ii) setting the radiation dose to be delivered to the target and limiting the radiation dose to the non-target tissue;
   (iii) assigning control points to the surface contours identified in (i),
   (iv) determining the angle of the beam of radiation, the orientation of the collimator, and the position of the patient support system at each control point,
   (v) assigning "wild card" points within the volume of the target tissue with the proviso that a "wild card" point is not assigned within the volume of any non-target tissue that is located wholly or partially within the target tissue,
   (vi) determining the path of motion when all control points and one or more "wild card" points, are connected and optimizing the weighting of each control point of radiation so as to provide a dose pattern of radiation within the target tissue and a sharp drop-off away from the boundary between the target tissue and any non-target tissue, and
   (vii) checking the resulting radiation dose distribution against a desired radiation dose distribution and adjusting the path of motion and the weightings of control points accordingly and, if needed, adding more control points,
   whereupon irradiation of a target tissue in a patient is planned.

9. The method of claim 8, wherein the at least one collimator of the system (a) shapes the beam of radiation to have a D-shaped cross-section, (b) maintains the central axis of the beam of radiation on or adjacent to the straight edge of the D-shaped cross-section of the beam of radiation, and (c) fully rotates the D-shaped cross-section of the beam of radiation in either direction, such that the straight edge of the D-shaped cross-section of the beam of radiation faces any direction during irradiation.

10. The method of claim 9, wherein the straight edge of the D-shaped cross-section of the beam of radiation is maintained tangentially to the surface contour identified in (i).

* * * * *